United States Patent
Berti et al.

(10) Patent No.: US 10,913,751 B2
(45) Date of Patent: Feb. 9, 2021

(54) 1,3-DIAZO-4-OXA-[3.3.1]-BICYCLIC DERIVATIVES, PROCESS FOR THEIR MANUFACTURE AND THEIR USE AS A MEDICAMENT, IN PARTICULAR FOR TREATING DIABETES

(71) Applicant: UNIVERSITA' DI PISA, Pisa (IT)

(72) Inventors: Francesco Berti, San Giuliano Terme (IT); Mauro Pineschi, Certaldo (IT); Andrea Menichetti, Leghorn (IT)

(73) Assignee: UNIVERSITA' DI PISA, Pisa (IT)

( * ) Notice: Subject to any disclaimer, the term of this patent is extended or adjusted under 35 U.S.C. 154(b) by 0 days.

(21) Appl. No.: 16/616,119

(22) PCT Filed: May 30, 2018

(86) PCT No.: PCT/IB2018/053834
§ 371 (c)(1),
(2) Date: Nov. 22, 2019

(87) PCT Pub. No.: WO2018/220542
PCT Pub. Date: Dec. 6, 2018

(65) Prior Publication Data
US 2020/0172552 A1 Jun. 4, 2020

(30) Foreign Application Priority Data
May 31, 2017 (IT) .................. 102017000059292

(51) Int. Cl.
C07D 498/08 (2006.01)
A61P 3/10 (2006.01)

(52) U.S. Cl.
CPC .............. *C07D 498/08* (2013.01); *A61P 3/10* (2018.01)

(58) Field of Classification Search
CPC .................................................. C07D 498/08
See application file for complete search history.

(56) References Cited

FOREIGN PATENT DOCUMENTS

| EP | 1231212 A1 | 8/2002 |
|----|------------|--------|
| WO | 2005042533 A2 | 5/2005 |
| WO | 2014193832 A2 | 12/2014 |

OTHER PUBLICATIONS

Search Report and Written Opinion of PCT/IB2018/053834 dated Jul. 30, 2017.
Stolz D. et al., "Aromatic nitro groups and their reactions with chelated ester enolates", Synthesis, vol. 2006, No. 19, Sep. 4, 2006, p. 3344.
Search Report and Written Opinon of priority Italian Patent Application No. 102017000059292 dated Dec. 4, 2017.

*Primary Examiner* — Susanna Moore
(74) *Attorney, Agent, or Firm* — Silvia Salvadori, P.C.; Silvia Salvadori

(57) ABSTRACT

The present invention relates to compounds having structural formula (I) wherein $R^1$ and $R^2$ are defined as set forth in the description. The invention also relates to a process for the manufacture of the above compounds of formula (I), wherein a 4a,7,8,8a-tetrahydropyrido[4,3-e]-1,4,2-dioxazine reacts with a hydride selected from the group consisting of: lithium triethylborohydride ($LiBHEt_3$), sodium triethylborohydride ($NaBHEt_3$), and lithium tetrahydroaluminate ($LiAlH_4$), in the presence of tetrahydrofuran. Furthermore, the invention is aimed at the above compounds of formula (I), or pharmaceutically acceptable salts thereof, for use in medicine, preferably in the treatment of the diabetes and pathologies or conditions correlated thereto.

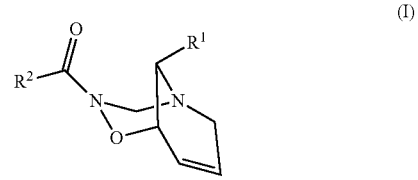

16 Claims, 1 Drawing Sheet

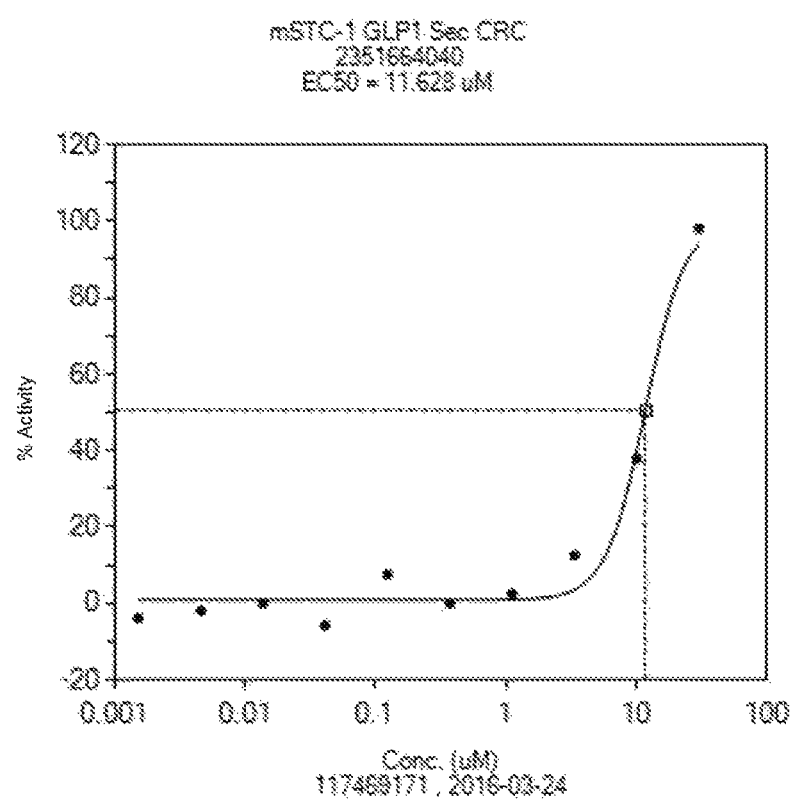

1,3-DIAZO-4-OXA-[3.3.1]-BICYCLIC DERIVATIVES, PROCESS FOR THEIR MANUFACTURE AND THEIR USE AS A MEDICAMENT, IN PARTICULAR FOR TREATING DIABETES

This application is a U.S. national stage of PCT/IB2018/053834 filed on 30 May 2018 which claims priority to and the benefit of Italian patent application No. 102017000059292 filed on 31 May 2017, the content of which are incorporated herein by reference in their entireties.

TECHNICAL FIELD

The present invention relates to 1,3-diazo-4-oxa-[3.3.1]-bicyclic derivatives, a process for their manufacture and their use as a medicament, in particular for treating diabetes and pathologies or conditions correlated thereto.

STATE OF THE ART

The Diels-Alder reaction has long been widely used in organic synthesis and consists in a cycloaddition between a conjugated diene and a dienophile, which leads to the formation of substituted cyclohexanes. Diels-Alder reactions that involve at least one heteroatom are collectively called "hetero-Diels-Alder" reactions; in particular, in a "nitroso-Diels-Alder" reaction (NDA) the nitroso group (R—N=O acts as a dienophile and the cycloaddition leads to the introduction of nitrogen and oxygen at the 1-4 positions of a 1,3-diene, with the formation of oxazines.

The use of 1,2-dihydropyridine as conjugated dienes in the acyl-nitroso-Diels-Alder reaction has never received particular attention, although it offers the advantage of stereoselectively introducing a new carbon-oxygen bond and a new carbon-nitrogen bond on the pyridine skeleton, thus regioselectively forming the corresponding reverse nitroso cycloadduct of the general formula (1), as shown in diagram 1 below (PG=protective group).

In some studies (Knaus et al., J. Org. Chem, 1985; Streith et al., Tetrahedron Lett., 1990) it was reported that the hetero-Cope [3,3] rearrangement of benzoylnitroso cycloadducts ((1), where $R^1$=H, $R^2$=Ph, PG=COOMe) led to the corresponding 4a,7,8a-tetrahydropyrido[4,3-e]-1,4,2-dioxazine ((2), where $R^2$=Ph, diagram 1). However, in such studies the reaction conditions of the rearrangement were either not very well defined (Streith et al.) or very long reaction times were necessary in order for the rearrangement to take place (up to 15 days, Knaus et al.). Precisely because of this difficulty in synthesising them, despite the potential usefulness for purposes of chemical synthesis, dioxazines (2) have not been particularly exploited as building blocks.

Diagram 1

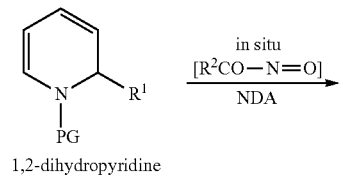

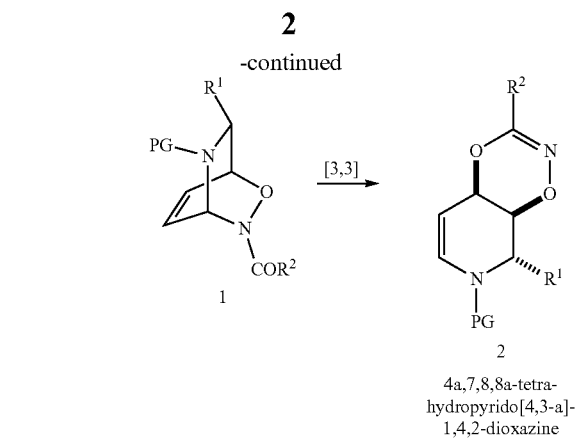

4a,7,8,8a-tetra-hydropyrido[4,3-a]-1,4,2-dioxazine

Incretins are a group of peptide hormones that stimulate a reduction in blood glucose levels. Incretins are produced by the enteroendocrine cells located in the gastrointestinal tract (in particular in the ileum, colon and duodenum) in response to the ingestion of nutrients and introduced into the bloodstream. These hormones have the function of controlling the blood glucose level (glycaemia) in various ways, in particular (i) by increasing the secretion of insulin by the beta cells of the pancreas; (ii) by decreasing the secretion of glucagon by the alpha cells of the pancreas; and (iii) by slowing motility and hence gastric emptying and decreasing appetite.

The therapeutic relevance of incretins has grown rapidly in recent years and one of the most studied incretins is GLP-1 (glucagon-like peptide-1), produced by L-type enteroendocrine cells (L-cells). GLP-1 integrates the signals deriving from nutrients in order to control food intake, energy absorption and assimilation. Several recently approved drugs based on enhancement of the action of incretins provide new approaches for the physiological treatment of type 2 diabetes and problems such as obesity associated with the use of traditional antidiabetics like insulin, sulphonylureas or thiazolidinediones. Exenatide and liraglutide are first-generation GLP-1 receptor agonists which, being peptides, require parenteral administration once or twice a day. Therefore, research in this field is still constantly active.

The present invention thus aims to provide new compounds that are effective in the treatment of diabetes and pathologies or conditions correlated thereto. In particular, the invention pursues the object of providing new compounds capable of modulating the GLP-1 receptor; another object of the invention is to provide compounds capable of modulating the GLP-1 receptor and which can be orally administered. Moreover, the invention has the object of providing a process for the manufacture of such compounds and in particular it aims to define the reaction conditions for carrying out the process in a rapid, simple and economically advantageous manner.

OBJECT OF THE INVENTION

The present invention relates to compounds having the following structural formula (I):

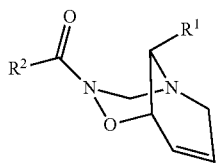
(I)

wherein:

R¹ is selected from the group consisting of: H, $C_1$-$C_6$ alkyl, vinyl, allyl, cyclohexyl, 1,2,3-triazole, phenyl optionally substituted by a halogen or by a methoxy functional group, C≡C-Ph, and —$CH_2$—$COOCH_3$; and R² is selected from the group consisting of:

(i) phenyl or benzyl, optionally substituted by one or more functional groups independently selected from the group consisting of a halogen, a methoxy functional group and —$CF_3$;

(ii) isoxazole;

(iii) pyrrole;

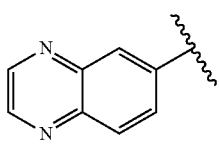
(iv)

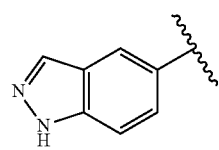
(v)

(vi)

(vii)

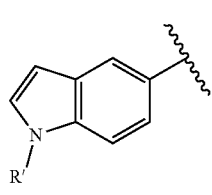
(viii)

wherein R' is H or methyl

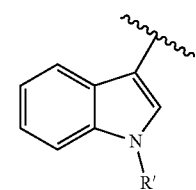
(ix)

wherein R' is H or methyl

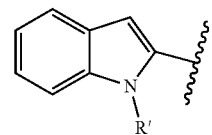

wherein R' is H or methyl

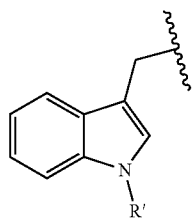
(x)

wherein R' is H or methyl

The invention also relates to a process for the manufacture of the compounds having the aforesaid formula (I) by reaction of a 4a,7,8,8a-tetrahydropyrido[4,3-e]-1,4,2-dioxazine having formula (2):

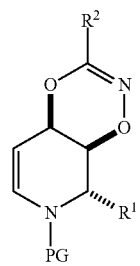
(2)

wherein R¹ and R² are as defined for the structure (I) and PG is a protective group comprising a carboxylic functional group, with a hydride selected from the group consisting of: lithium triethylborohydride ($LiBHEt_3$), sodium triethylborohydride ($NaBHEt_3$), and lithium tetrahydroaluminate ($LiAlH_4$), in the presence of tetrahydrofuran, at a temperature comprised between 0° C. and room temperature for a time comprised between 15 minutes and 4 hours. The invention further relates to the compounds of the aforesaid formula (I), and the pharmaceutically acceptable salts thereof, for use as a medicament, in particular for the treatment of diabetes and pathologies or conditions correlated thereto.

BRIEF DESCRIPTION OF THE DRAWINGS

FIG. 1 shows the measurement by ELISA assay of the biological activity of the bicyclic compound with structure (Ib) as a GLP-1 receptor agonist (mSTC-1 GLP1 sec CRC).

DETAILED DESCRIPTION OF PREFERRED EMBODIMENTS OF THE INVENTION

From a chemical standpoint, the compounds of formula (I) according to the present invention are 1,3-diazo-4-oxa-[3.3.1]-bicyclic derivatives.

In one embodiment of the compounds of formula (I) disclosed herein, R¹ can preferably be selected from the group consisting of hydrogen and phenyl, optionally substituted by a halogen or by a methoxy functional group.

In another embodiment, R¹ can be selected from the group consisting of vinyl, allyl and cyclohexyl.

In another embodiment, R¹ is selected from the group consisting of $C_1$-$C_6$ alkyl, preferably $C_1$-$C_3$ alkyl.

In another embodiment, R¹ is 1,2,3-triazole.

In a preferred embodiment, when R¹ is a phenyl substituted by a halogen, said halogen can preferably be selected between chlorine and fluorine. Furthermore, said halogen can preferably be in the para (p-) position of the phenyl relative to the core of the molecule.

Similarly, when $R^1$ is a phenyl substituted by a methoxy group, said methoxy group can preferably be in the para (p-) position of the aromatic ring.

In one embodiment of the compounds of formula (I) disclosed herein, $R^2$ can preferably be a phenyl or a benzyl and said phenyl or benzyl can optionally be substituted by one or more functional groups independently selected from among: a halogen, a methoxy functional group and $-CF_3$.

In a preferred embodiment, $R^2$ can be an unsubstituted phenyl or benzyl.

In another preferred embodiment, $R^2$ can be a phenyl or a benzyl, wherein said phenyl or benzyl are substituted by a single functional group selected from among: halogen, methoxy and $-CF_3$; more preferably, the functional group is selected from among: halogen, methoxy and $-CF_3$ can be in the position para (p-) or in the position meta (m-) of the aromatic ring.

In another preferred embodiment, when $R^2$ is a phenyl or a benzyl substituted by a halogen, said halogen can preferably be selected between chlorine and fluorine.

In another embodiment, $R^2$ can have a structural formula selected from the group consisting of:

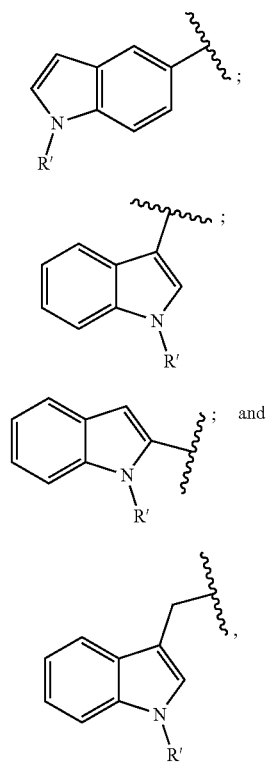

wherein R' is H or methyl.

The structural formulas indicated here as (vii), (viii) and (ix) all refer to an indole, optionally substituted by a methyl on the nitrogen atom.

In a preferred embodiment, when $R^2$ has a structural formula selected from among (vii), (viii), (ix) and (x) as defined above, R' can preferably be hydrogen. More preferably, when $R^2$ has a structural formula selected from among (vii), (ix) and (x) as defined above, R' can preferably be hydrogen.

In one embodiment of the compounds of formula (I), $R^1$ can be phenyl, optionally substituted by a halogen or by the methoxy functional group, and $R^2$ can be selected from the group consisting of phenyl and benzyl, wherein said phenyl or benzyl are optionally substituted by a halogen or by the methoxy functional group. More preferably, $R^2$ can be benzyl, optionally substituted by a halogen or by the methoxy functional group.

In another embodiment of the compounds of formula (I), $R^1$ can be phenyl, optionally substituted by a halogen or by the methoxy functional group, and $R^2$ can be selected from the group consisting of:

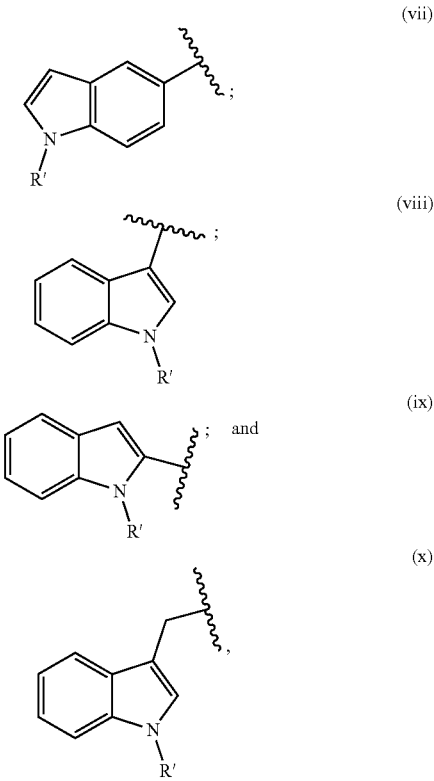

wherein R' is H or methyl (preferably H).

In another embodiment of the compounds of formula (I), $R^1$ can be phenyl, optionally substituted by a halogen or by the methoxy functional group, and $R^2$ can be pyrrole. In this embodiment, $R^1$ can preferably be unsubstituted phenyl or phenyl substituted by a halogen.

In one particularly preferred embodiment, the compounds of formula (I) can be selected from among those having the following formulas:

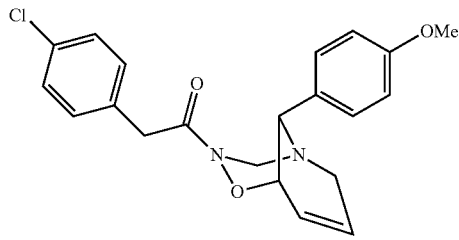

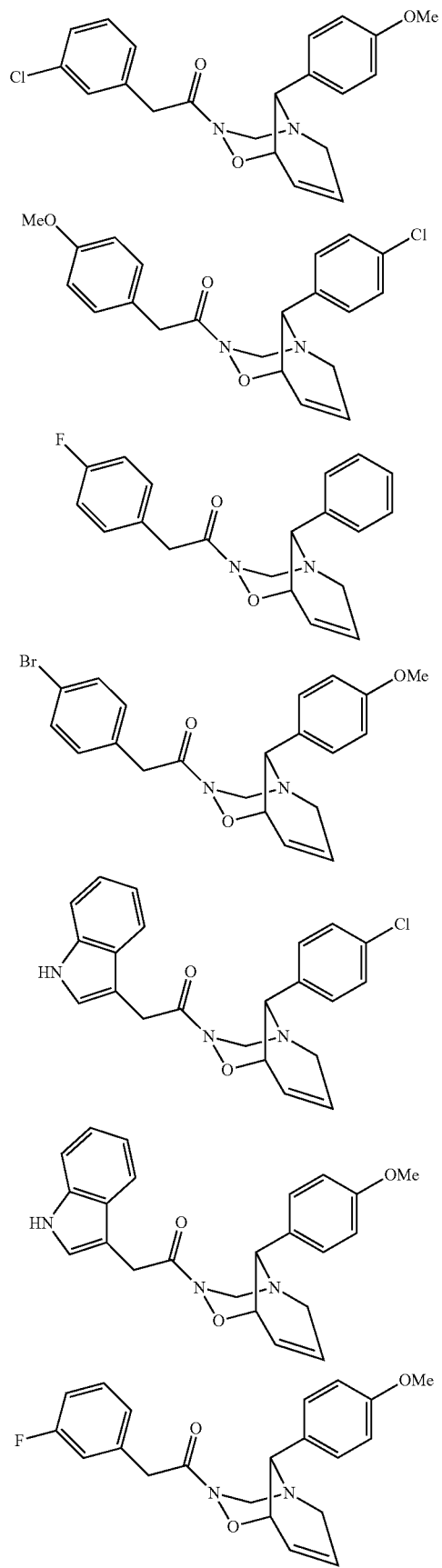
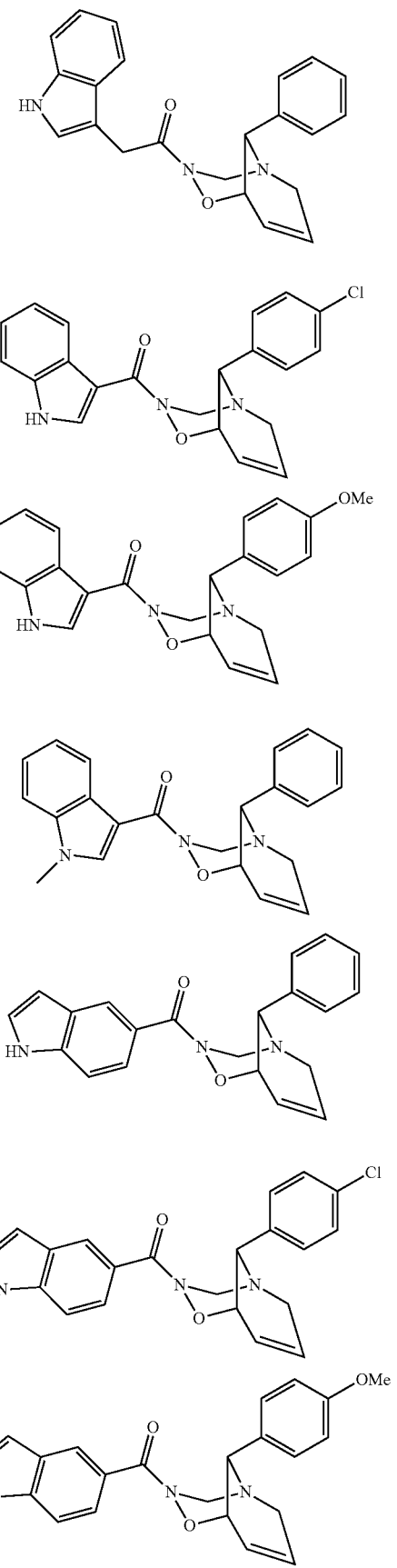

-continued
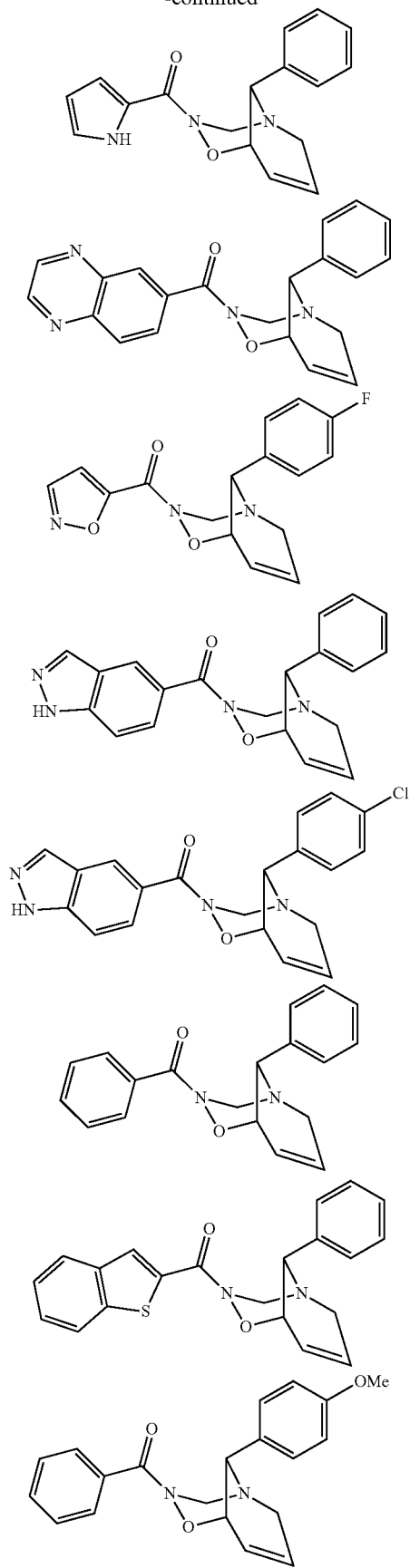
-continued
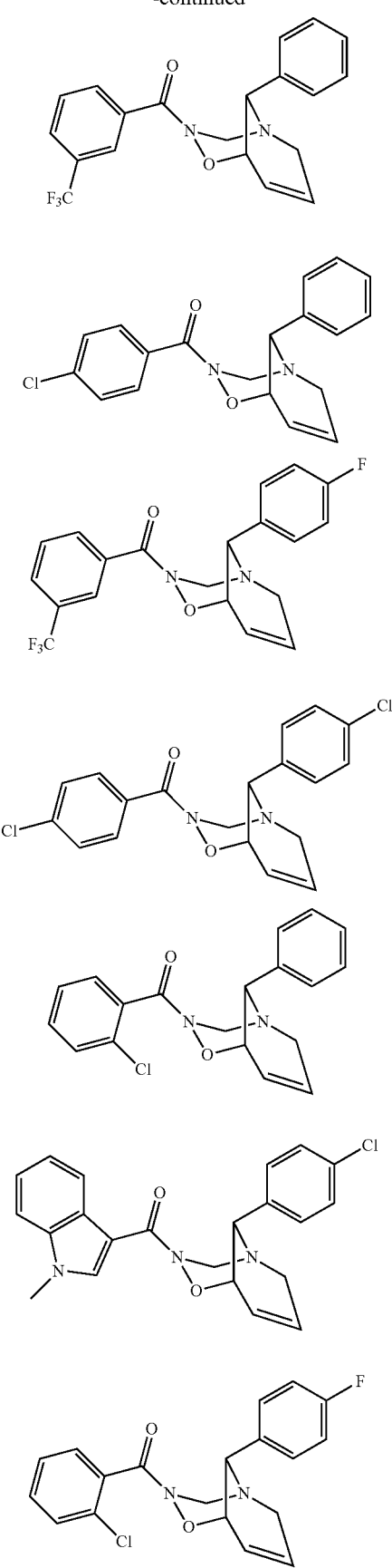

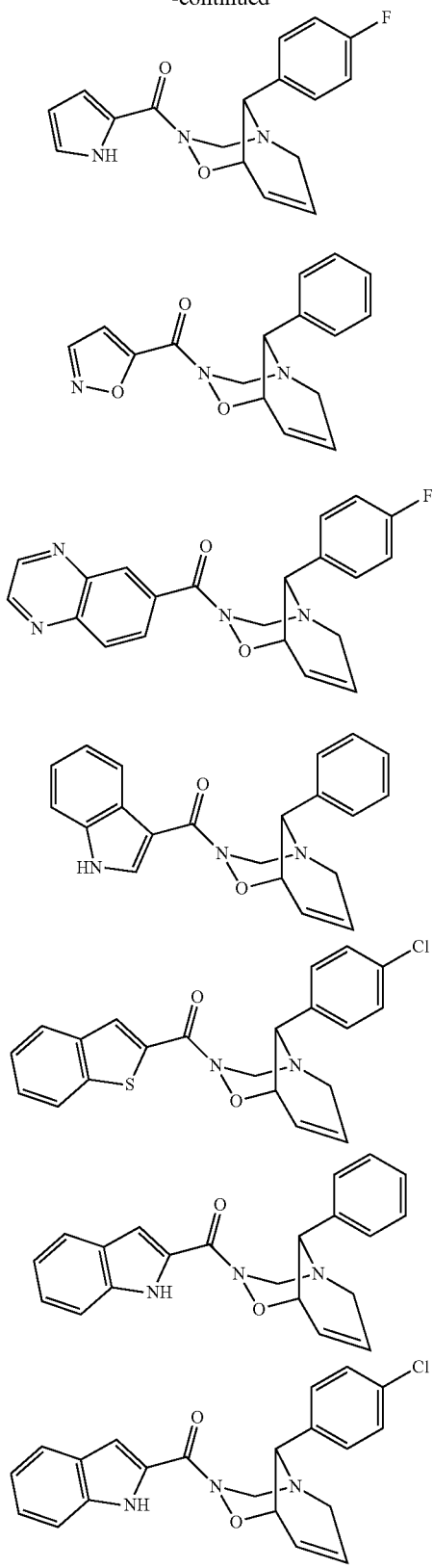
In an even more preferred embodiment, the compounds of formula (I) can be selected from among those having the following formulas:
These compounds correspond respectively (in the listed order) to the ones indicated in the examples that follow as (Ib), (If), (Ia), (Im), (In), (Io), (Ip).
Even more preferably, the compound of formula (I) can have the following formula:

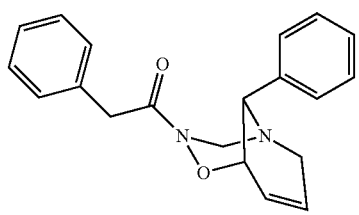

In this structure, the substituent $R^1$ is an unsubstituted phenyl and the substituent $R^2$ is an unsubstituted benzyl; this compound corresponds to the structure indicated in the present description as (Ib).

Another aspect of the invention relates to a process for the manufacture of the compounds of formula (I) disclosed herein, wherein a 4a,7,8,8a-tetrahydropyrido[4,3-e]-1,4,2-dioxazine having formula (2):

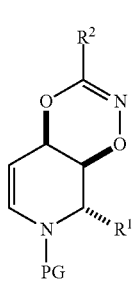

(2)

wherein $R^1$ and $R^2$ are as defined in reference to the structure (I) and PG is a protective group comprising a carboxylic functional group (COO—), is reacted with a hydride selected from the group consisting of: lithium triethylborohydride (LiBHEt$_3$), sodium triethylborohydride (NaBHEt$_3$), and lithium tetrahydroaluminate (LiAlH$_4$), in the presence of tetrahydrofuran, at a temperature comprised between 0° C. and room temperature for a time comprised between 15 minutes and 4 hours.

In a preferred embodiment, the process can be carried out at a temperature of 0° C. (±1° C.). In another preferred embodiment, the process can be carried out at room or ambient temperature: standard ambient temperature (SAT) means a temperature of 25° C. (±1° C.), as is well known in the field of chemistry.

In a preferred embodiment, the hydride which reacts with the dioxazine can be lithium triethylborohydride (LiBHEt$_3$ or LiTEBH); lithium triethylborohydride is a commercially available hydride known by the trade name Super-hydride®.

In another preferred embodiment, the process of the invention can take place in the presence of a palladium-based catalyst comprising at least one triphenylphosphine group. Advantageously, the catalyst can be selected from the group consisting of: tetrakis(triphenylphosphine)palladium (0) (Pd(PPh$_3$)$_4$) and bis(triphenylphosphine)palladium(II) dichloride ((PPh$_3$)$_2$PdCl$_2$). More preferably, the catalyst can be (PPh$_3$)$_2$PdCl$_2$.

In one embodiment, the process can take place using the hydride LiBHEt$_3$, in the absence of a catalyst and at a temperature of 0° C. (±1° C.). In another embodiment, the process can take place in the absence of a catalyst and at room temperature. In another embodiment, the process can take place in the presence of a catalyst and at a temperature of 0° C. (±1° C.).

The reaction time can range between about 15 minutes and about 4 hours, depending on the other reaction conditions (above all temperature and the presence or absence of a catalyst) and the hydride used. The time taken can preferably be comprised between about 20 minutes and about 60 minutes when LiBHEt$_3$ is used, irrespective of whether the catalyst is present. NaBHEt$_3$ is less effective and when it is used in the process longer reaction times are necessary, preferably comprised between 2 hours and 30 min and 3 hours and 30 min, depending on whether the catalyst is present or not.

In order to succeed in defining the conditions of the process of the invention, the inventors assessed the behaviour of the dioxazine of formula (2) where $R^1$=Ph, $R^2$=CH$_2$Ph and PG=COOMe under reducing conditions and different reaction conditions. This dioxazine will hereinafter be indicated as (2b).

The reaction of the dioxazine (2b) is shown in Diagram 2 below.

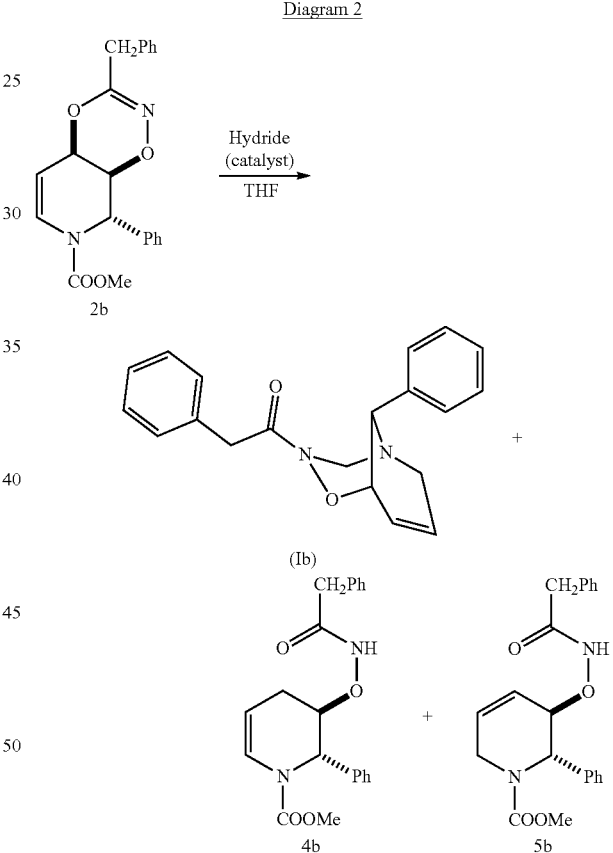

Diagram 2

The various experimental conditions examined and the respective results obtained in terms of products are shown in Table 1 below.

TABLE 1

| Example | Hydride | Catalyst | Temperature | Time | Ib/4b/5b[a] (%) |
|---|---|---|---|---|---|
| 1 (comparative) | NaBH$_4$ | none | 0° C. | 12 h | no reaction |

TABLE 1-continued

| Example | Hydride | Catalyst | Temperature | Time | Ib/4b/5b[a] (%) |
|---|---|---|---|---|---|
| 2 (comparative) | LiBH$_4$ | none | room | 18 h | 0/100/0[b] |
| 3 | LiBHEt$_3$ | none | 0° C. | 20 min | 100/0/0 |
| 4 | NaBHEt$_3$ | none | room | 3.5 h | 100/0/0 |
| 5 (comparative) | NaBH$_4$ | (PPh$_3$)$_2$PdCl$_2$ | 0° C. | 21 h | 0/50/50 |
| 6[c] (comparative) | NaBH$_4$ | (PPh$_3$)$_2$PdCl$_2$ | 60° C. | 24 h | no reaction |
| 7 (comparative) | LiBH$_4$ | (PPh$_3$)$_2$PdCl$_2$ | 0° C. | 1 h | 0/72/28 |
| 8 | LiBHEt$_3$ | (PPh$_3$)$_2$PdCl$_2$ | 0° C. | 30 min | 95/5/0 |
| 9 | LiAlH$_4$ | (PPh$_3$)$_2$PdCl$_2$ | 0° C. | 30 min | 95/5/0 |
| 10 | NaBHEt$_3$ | (PPh$_3$)$_2$PdCl$_2$ | 0° C. | 3 h | 95/5/0 |
| 11 | LiBHEt$_3$ | Pd(PPh$_3$)$_4$ | 0° C. | 30 min | 95/5/0 |
| 12 (comparative) | LiBHEt$_3$ | Pd(dba)$_2$ | 0° C. | 1 h | 37/63/0 |
| 13 (comparative) | LiBHEt$_3$ | Pd(CH$_3$CN)$_2$Cl$_2$ | 0° C. | 30 min | 0/100/0[b] |
| 14 (comparative) | LiBHEt$_3$ | Pd(CH$_3$CN)$_2$Cl$_2$ | −78° C. | 2 h | no reaction |
| 15 (comparative) | NaBHEt$_3$ | Pd(CH$_3$CN)$_2$Cl$_2$ | 0° C. | 40 min | 0/100/0[b] |
| 16[d] (comparative) | NaBH$_4$ | Pd(CH$_3$CN)$_2$Cl$_2$ | 0° C. | 48 h | 0/100/0 |

[a] determined by NMR analysis;
[b] a further unidentified product was recovered;
[c] reaction conducted in MeOH
[d] the conversion was 60%

With reference to the test results shown in table 1 above, an assessment was first made of the effects of using hydrides having a different strength and of the presence or absence of palladium-based catalysts having different electronic characteristics. Reactions were initially conducted in the absence of a palladium-based catalyst in order to exclude the triggering of secondary reactions promoted by the hydrides.

The first hydride examined was sodium borohydride; the dioxazine (2b) treated with sodium borohydride in THF for 12 hours did not undergo any reaction. The use of lithium borohydride resulted in the obtainment of a secondary product, a piperidine of structure (4b) (see reaction Diagram 2 above). When lithium borohydride was replaced with 6 equivalents of lithium triethylborohydride (Super-hydride®, a stronger hydride), the reaction led to the obtainment of the 1,3-diazo-4-oxa-[3.3.1]-bicyclic derivative of structure (Ib). Furthermore, it was noted that it was also possible to obtain the derivative of structure (Ib) using sodium triethylborohydride, though a longer reaction time and higher temperature were necessary than when lithium triethylborohydride was used.

The reaction mechanism seems to involve a non-catalysed initial S$_N$2' type reaction of the hydride at the C6 position of the dioxazine, which is followed by the opening of the dioxazine structure and subsequent intramolecular amination, as shown in diagram 3 below, which makes reference to the reaction of the dioxazine (2b).

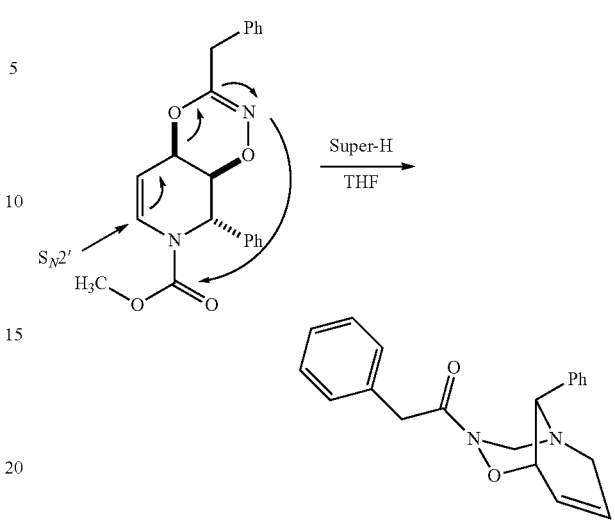

Diagram 3

It should be said that, whilst the allylic deoxygenation reaction catalysed by palladium is known in the prior art, a non-catalysed S$_N$2' type reaction between a hydride and a substrate, such as the dioxazine of structure (2), which comprises a piperidine bearing a leaving allyl group has not been reported to date.

An assessment was thus made of how palladium could influence the reaction. It was observed from the tests carried out, the results of which are likewise shown in table 1, that 6 equivalents of sodium borohydride gave a mixture of unsaturated piperidine having structures (4b) and (5b) in a ratio similar to that resulting from the use of the catalyst bis(triphenylphosphine)palladium(II) dichloride (example 5). This different result compared with the control reaction supports the formation of a β-allyl complex.

The solvent is also essential in order for the reaction to take place: carrying out the reaction in methanol does not lead to any product, even when the temperature is raised to 60° C. (example 6).

When the dioxazine (2b) is treated with lithium borohydride, the ratio between the piperidine of structures (4b) and (5b) varies slightly (example 7). In contrast, the compound (Ib) according to the invention proved to be the predominant product when the reaction was carried out with bis(triphenylphosphine)palladium(II) dichloride and lithium triethylborohydride (example 8). Analogously, the lithium tetrahydroaluminate reacted rapidly with the dioxazine (2b) to yield the compounds of structures (Ib) and (4b) in a 95:5 ratio (example 9). The same regioselectivity was obtained using sodium triethylborohydride (example 10).

Based on the data provided in table 1, which show that the regioselectivity of the reaction leads to compound (Ib) or products (4b) and/or (5b) depending on the reaction conditions, the inventors have concluded that two distinct reactions can take place. The first is an S$_N$2/S$_N$2' reaction mediated by hydrides comprising lithium as the counterion; the second is an allylic substitution catalysed by palladium. Both reactions take place starting from an initial addition on the enecarbamate portion of the dioxazine (2b). Therefore, when the reaction conditions provide for a lithium-based hydride and a palladium-based catalyst, the two reactions compete for the substrate (2b) and, as a consequence, the ratio of the products obtained ((Ib) and (4b)/(5b)) depends on the respective speed of the two reactions.

The protective group PG bonded to nitrogen has an important role in the preparation of 1,3-diazo-4-oxa-[3.3.1]-bicyclic derivatives with the process according to the invention. The inventors have determined that the protective group must be such as to form a carbamate following the formation of the bond with the nitrogen atom present on the oxazolic ring of the dioxazine, according to the mechanism shown above in reaction diagram 3. The presence of the carbamate is in fact an essential condition in order to have reactivity with the hydrides. In order for the protective group to form a carbamate by reacting with the nitrogen of the oxazolic ring, it must comprise a carboxylic group (COO—). By way of example, some appropriate protective groups can be —COOMe, —COOPh and —CBz.

Table 2 below shows the results of the rearrangement, according to the invention, of several dioxazines, achieved using LiBHEt$_3$ as a hydride and working in THF at 0° C.

The dioxazines indicated in table 2 were prepared in accordance with the invention, as described further below, and their structural formulas are shown in section 2.1 of the examples.

As may be observed, the reaction of the dioxazine (2f), wherein the substituent R$^1$ is an ethyl group, gave the corresponding compound (If) (example 1), even though a lower yield was found compared to the previously reported reaction of the dioxazine (2b). In contrast, the dioxazine (2h), where the protective group used was an acetyl, did not result in the expected compound (Ih): rather, a complex mixture of products was recovered (example 2). These results have thus demonstrated the necessary presence of a carbamate group (which forms when the protective group PG comprises a carboxyl) in order for the rearrangement leading to the corresponding 1,3-diazo-4-oxa-[3.3.1]-bicyclo to take place.

Furthermore, it was found that the dioxazines wherein R$^2$ is phenyl also underwent a rearrangement with the formation of the respective bicyclo of structure (I) (see example 5, where the dioxazine is (2m)): this result therefore offers the possibility of exploiting different dioxazines bearing an aryl group as the substituent R$^2$.

TABLE 2

| Example | PG | R$^1$ | R$^2$ | dioxazine | product |
|---|---|---|---|---|---|
| 1 | COOMe | Et | CH$_2$Ph | 2f | If |
| 2 (comparative) | COMe | Ph | CH$_2$Ph | 2h | Complex mixture |
| 3 | COOPh | H | CH$_2$Ph | 2a | Ia |
| 4 | CBz | H | CH$_2$Ph | 2d | Ia |
| 5 | COOMe | Ph | Ph | 2m | Im |
| 6 | COOMe | (Vinyl) C$_2$H$_3$ | CH$_2$Ph | 2n | In |
| 7 | COOMe | (Cyclohexyl) Chx | CH$_2$Ph | 2o | Io |
| 8 | COOMe | (Allyl) CH2=CH—CH2— | CH$_2$Ph | 2p | Ip |

In one embodiment, the process of the invention can also comprise a step, preceding the reaction of the dioxazine of formula (2) with the hydride, wherein the dioxazine itself is obtained by a [3,3]-sigmatropic type rearrangment starting from the corresponding reverse cycleadduct. The cycleadducts corresponding to the dioxazines of formula (2) which react in the process of the invention have the formula (1) shown below in reaction diagram 4, wherein R$^1$ and R$^2$ have the meanings previously defined for the compounds of formula (I) and the dioxazines of formula (2).

Diagram 4

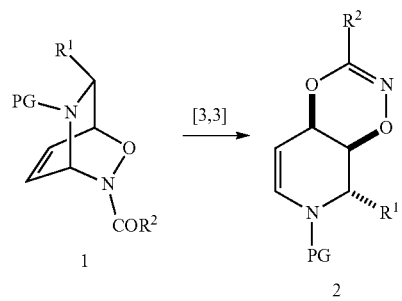

Although this reaction is known in the prior art, the inventors were able to define conditions that allow the reaction to take place effectively and with reasonable reaction times. Therefore, the rearrangement of the cycleadduct according to the present invention takes place in dichloroethane, at a temperature of 75° C. (±2° C.) and in the presence of CuCl as a catalyst. Preferably, the amount of CuCl can be comprised between 18 mol % and 22 mol %, more preferably it can be equal to 20 mol %.

In another aspect, the invention relates to the compounds having structural formula (I), wherein R$^1$ and R$^2$ are defined as set forth above, or pharmaceutically acceptable salts thereof, for use as a medicament. The inventors have in fact found that the compounds of formula (I) are capable of modulating, in a direct or indirect manner, the GLP-1 receptor. The compounds of the invention thus act upon the mechanism of signal transmission (pathway) mediated by the GLP-1 receptor. By virtue of this action, the compounds of the invention or the pharmaceutically acceptable salts thereof can be used in particular to treat diabetes, preferably type 2 diabetes. Furthermore, the compounds of the invention or the pharmaceutically acceptable salts thereof can be used in the treatment of several pathologies correlated to diabetes, such as obesity and dyslipidaemic syndromes. The term "dyslipidaemic syndromes" (or "dyslipidaemias") refers generically to conditions in which the amount of lipids (in particular cholesterol, triglycerides and/or phospholipids) in the bloodstream is altered compared to the normal physiological condition; in dyslipidaemias the amount of lipids is increased (hypercholesterolaemia, hypertriglyceridaemia, hyperphospholipidaemia), but there also exist dyslipidaemias in which the amount of lipids is lower than in normal physiological condition. One complication typical of dyslipidaemic syndromes is represented by hepatic steatosis (commonly called "fatty liver"), in which there is an intracellular accumulation of lipids in hepatic tissue: hepatic steatosis can be treated by means of the compounds of the present invention or the pharmaceutically acceptable salts thereof. Moreover, the compounds of the invention or the pharmaceutically acceptable salts thereof can also be used to regulate the sense of satiety or appetite.

The compounds of formula (I) according to the present invention, the process for their manufacture and their use for treating diabetes and the pathologies or conditions associated therewith, conceived as described herein, are susceptible of numerous modifications and variants, all falling within the scope of the inventive concept; furthermore, all of the details may be replaced by other equivalent elements whose correspondence is known to the person skilled in the art.

Furthermore, it is to be understood that the characteristics of the embodiments described with reference to one aspect of the invention are to be considered valid also in relation to other aspects of the invention, even if not explicitly repeated.

The invention will now be illustrated by some examples whose purpose is absolutely not to be construed as limiting the scope of protection.

EXAMPLES

1. Materials and Methods

All the commercially available reagents were purchased except where specified otherwise. The solvents for extraction and chromatography were distilled prior to use. All of the reactions involving compounds sensitive to air or humidity were carried out in an argon atmosphere in 10 ml or 25 ml Schlenk tubes oven dried in advance.

The TLC analyses were carried out on Alugram SIL G/UV254 silica gel sheets with detection by exposure to ultraviolet light (254 nm) and/or per immersion in an acid staining solution of p-anisaldehyde in EtOH. For the flash chromatography, silica gel 60 was used (Macherey-Nagel 230-400 mesh).

The $^1$H NMR spectra were recorded on a Bruker Avance II 250 spectrometer. The chemical shifts are reported in ppm relative to tetramethylsilane considering the resonance of the solvent as an internal standard (deuterochloroform: $\delta7.26$, deuteroacetonitrile: $\delta1.94$). The $^{13}$C NMR spectra were recorded on a Bruker Avance II 250 spectrometer (62.5 MHz) with complete proton decoupling. The chemical shifts are reported in ppm relative to tetramethylsilane considering the resonance of the solvent as an internal standard (deuterochloroform: $\delta77.16$, deuteroacetonitrile: $\delta1.32$).

The melting points were determined with a Kofler unit and were not corrected.

The HRMS (ESI) mass spectra were measured with a Q-TOF spectrometer with a nanoelectrospray ion source.

The biological activity of the synthesised compounds was measured with an ELISA assay.

2. Preparation of the Dioxazines (According to Reaction Diagram 4)

2.1 General Synthesis Procedure

The specific reverse cycleadduct of formula (1), copper chloride (I) (CuCl, 0.20 equivalents) and 1,2-dichloroethane (DCE, 0.15 M) were introduced into a 10 ml oven-dried Pyrex vial. The resulting mixture was left to react until the TLC analysis no longer revealed any starting reagent. The reaction was quenched with water, the aqueous phase was extracted with $CH_2Cl_2$ and the combined organic layers were dried on $MgSO_4$. The removal of the solvent gave a residue that was purified by flash chromatography.

Shown below are some dioxazines (2a-2p) prepared starting from a corresponding reverse cycleadduct of formula (1) according to the reaction shown in diagram 4.

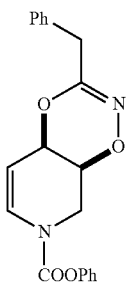

2a

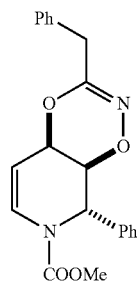

2b

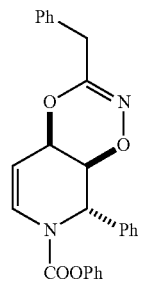

2c

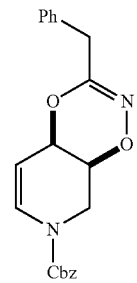

2d

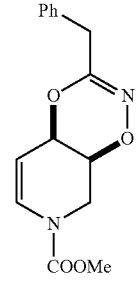

2e

-continued
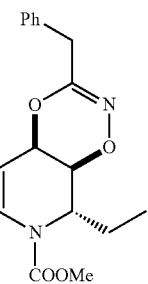
2f
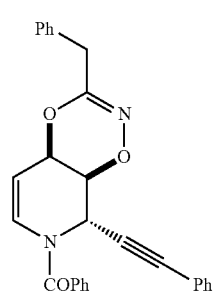
2g
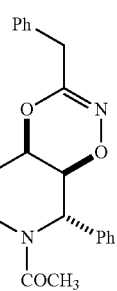
2h
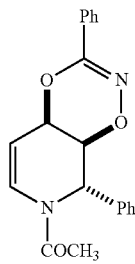
2i
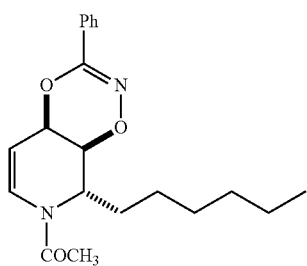
2j
-continued
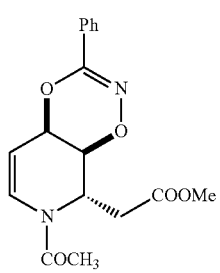
2k
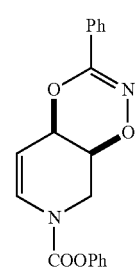
2l
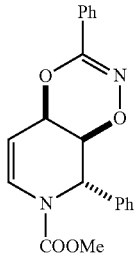
2m
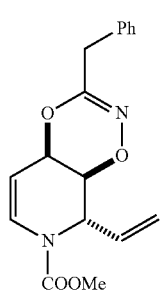
2n
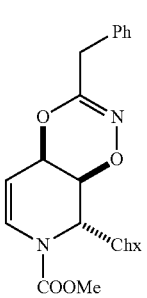
2o -continued 2p

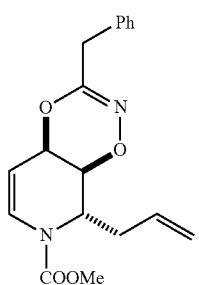

(4aR*,8aS*)-phenyl 3-benzyl-8,8a-dihydropyrido[4,3-e][1,4,2] dioxazine-7(4aH)-carboxylate (2a)

As described in the general procedure, the cycleadduct (1a) (70.1 mg, 0.20 mmol) and CuCl (4.0 mg, 0.04 mmol) reacted in DCE (1.32 ml) at 75° C. for 18 h. The subsequent flash chromatography (hexane/AcOEt 7:3, Rf=0.34) led to the above compound, in semisolid form (40 mg, 59%).

$^1$H NMR (250 MHz, CD$_3$CN, 65° C.) δ 7.47-7.23 (m, 8 H), 7.22-7.14 (m, 2 H), 7.06 (d, 1 H, J=6.3 Hz), 4.95-4.86 (m, 2 H), 4.26-4.19 (m, 1 H), 4.11-3.98 (m, 1 H), 3.85-3.69 (m, 1 H), 3.51 (s, 2 H).

$^{13}$C NMR (62.5 MHz, CD$_3$CN) δ 156.0, 153.1, 152.5* and 152.0, 136.9, 130.4, 129.7, 129.5, 128.7* and 128.6, 127.9, 126.9, 122.8, 103.9* and 103.3, 67.3 and 67.2*, 65.3* and 65.2, 44.0* and 43.7, 38.7. [*minor rotamer].

HRMS (ESI) m/z [M+Na$^+$] calculated for C$_{20}$H$_{18}$N$_2$O$_4$Na 373.1164, found 373.1161.

(4aR*,8S*,8aS*)-methyl 3-benzyl-8-phenyl-8,8a-dihydropyrido[4,3-e][1,4,2] dioxazine-7(4aH)-carboxylate (2b)

As described in the general procedure, the cycleadduct (1b) (73 mg, 0.20 mmol) and CuCl (4.0 mg, 0.04 mmol) reacted in DCE (1.32 mL) at 75° C. for 15 h. The subsequent flash chromatography (hexane/AcOEt 8:2+1% Et$_3$N, Rf=0.11) led to the above compound, in white solid form (55 mg, 75%). Melting point=45-48° C.

$^1$H NMR (250 MHz, CD$_3$CN, 65° C.) δ 7.42-7.21 (m, 10 H), 7.17-7.10 (m, 1 H), 5.46 (d, 1 H, J=2.9 Hz), 4.77-4.70 (m, 1 H), 4.55-4.50 (m, 1 H), 4.19-4.14 (m, 1 H), 3.70 (s, 3 H), 3.48 (s, 2 H).

$^{13}$C NMR (62.5 MHz, CDCl$_3$) $^{13}$C NMR (62.5 MHz, CDCl$_3$) δ 156.5, 151.2, 136.9 and 136.8*, 130.1, 130.0, 129.6, 129.5, 129.1, 128.1* and 127.9, 126.6, 122.4, 102.4, 69.0, 66.4, 58.7, 54.2.

HRMS (ESI) m/z [M+Na$^+$] calculated for C$_{21}$H$_{20}$N$_2$O$_4$Na 387.1321 found 387.1322.

(4aR*,8S*,8aS*)-phenyl 3-benzyl-8-phenyl-8,8a-dihydropyrido[4,3-e][1,4,2] dioxazine -7(4aH)-carboxylate (2c)

As described in the general procedure, the cycleadduct (1c) (85 mg, 0.20 mmol) and CuCl (4.0 mg, 0.04 mmol) reacted in DCE (1.32 ml) at 75° C. for 18 h. The subsequent flash chromatography (hexane/AcOEt 7:3, Rf=0.12) led to the above compound, in semisolid form (36 mg, 42%).

$^1$H NMR (250 MHz, CD$_3$CN) δ 7.47-7.19 (m, 14 H), 7.03 (d, 2 H, J=7.3 Hz), 5.62 (d, 1 H, J=2.7 Hz), 4.88 (dt, 1 H, J=8.6, 2.1 Hz), 4.61 (dt, 1 H, J=3.6, 1.9 Hz), 4.28-4.22 (m, 1 H), 3.51 (s, 2 H).

$^{13}$C NMR (62.5 MHz, CD$_3$CN) δ 156.9, 152.3, 137.2, 137.1, 130.6, 130.3, 129.9, 129.7, 129.5, 128.3, 128.1, 127.1, 127.0, 122.7, 104.2, 69.6, 66.8, 59.8, 38.8.

HRMS (ESI) m/z [M+Na$^+$] calculated for C$_{26}$H$_{22}$N$_2$O$_4$Na 449.1477 found 449.1479.

(4aR*,8aS*)-benzyl 3-benzyl-8,8a-dihydropyrido[4,3-e][1,4,2]dioxazine-7(4aH)-carboxylate (2d)

As described in the general procedure, the cycleadduct (1d) (845 mg, 2.3 mmol) and CuCl (45.5 mg, 0.46 mmol) reacted in DCE (15.2 mL) at 75° C. for 18 h. The subsequent flash chromatography (hexane/AcOEt 7:3, Rf=0.28) led to the above compound, in white solid form (268 mg, 32%). Melting point=68-72° C.

$^1$H NMR (250 MHz, CD$_3$CN, 65° C.) δ 7.46-7.25 (m, 1 0H), 6.92 (s, 1 H), 5.17 (s, 2 H), 4.91-4.69 (m, 2 H), 4.12 (s, 1 H), 3.94 (dd, 1 H, J=14.0, 5.4 Hz), 3.60 (t, 1 H, J=13.8 Hz), 3.46 (s, 2 H).

$^{13}$C NMR (62.5 MHz, CD$_3$CN) δ 155.8, 137.3, 136.9, 129.6, 129.5, 129.5, 129.2, 129.0, 128.6, 127.9, 102.7* and 102.2, 68.7, 67.3, 65.2, 43.4, 38.7. [*minor rotamer].

HRMS (ESI) m/z [M+Na$^+$] calculated for C$_{21}$H$_{20}$N$_2$NaO$_4$ 387.1321 found 387.1325.

(4aR*,8aS*)-methyl 3-benzyl-8,8a-dihydropyrido[4,3-e][1,4,2]dioxazine-7(4aH)-carboxylate (2e)

As described in the general procedure, the cycleadduct (1e) (54.0 mg, 0.19 mmol) and CuCl (3.7 mg, 0.037 mmol) reacted in DCE (1.23 ml) at 75° C. for 18 h. The subsequent flash chromatography (hexane/AcOEt 7:3+2% Et$_3$N Rf=0.20) led to the above compound, in white solid form (18 mg, 33%). Melting point=82-85° C.

$^1$H NMR (250 MHz, CDCl$_3$) δ 7.44-7.21 (m, 5 H), 7.06 (d, 1 H, J=7.7 Hz)* and 6.90 (d, 1 H, J=7.8 Hz), 4.92-4.69 (m, 2 H), 4.25-4.10 (m, 1 H), 4.05-3.87 (m, 1 H), 3.80 (s, 3 H), 3.67 (d, J=13.9 Hz, 1 H), 3.52 (s, 2 H).

$^{13}$C NMR (62.5 MHz, CDCl$_3$) δ 155.0, 153.9 and 153.6*, 135.4, 128.9, 128.7, 128.3, 127.2, 101.0 and 100.8*, 66.2 and 66.0, 64.9, 53.6, 42.2, 38.4. [*minor rotamer].

HRMS (ESI) m/z [M+Na$^+$] calculated for C$_{15}$H$_{16}$N$_2$O$_4$Na 311.1008 found 311.1007.

(4aR*,8S*,8aS*)-methyl 3-benzyl-8-ethyl-8,8a-dihydropyrido[4,3-e][1,4,2]dioxazine-7(4aH)-carboxylate (2f)

As described in the general procedure, the cycleadduct (1f) (63.3 mg, 0.20 mmol) and CuCl (4.0 mg, 0.04 mmol) reacted in DCE (1.32 ml) at 75° C. for 15 h. The subsequent flash chromatography (hexane/AcOEt 8:2+2% Et$_3$N, Rf=0.22) led to the above compound, in the form of an oil (33 mg, 52%).

$^1$H NMR (250 MHz, CD$_3$CN, 65° C.) δ 7.39-7.22 (m, 5 H), 6.82 (d, 1 H, J=8.5 Hz,), 4.93-4.88 (m, 1 H), 4.67 (dt, J=8.5, 2.1 Hz, 1 H), 4.36-4.25 (m, 1 H), 3.98 (dd, 1 H, J=5.8, 3.3 Hz), 3.75 (s, 3 H), 3.48 (s, 2 H), 1.63-1.43 (m, 2 H), 0.96 (t, 3 H, J=7.5 Hz).

$^{13}$C NMR (62.5 MHz, CD$_3$CN, 65° C.) δ 156.6, 154.8, 137.0, 129.7, 129.5, 127.9, 126.9, 101.9, 67.3, 66.5, 56.8, 53.9, 38.7, 23.2, 10.6.

HRMS (ESI) m/z [M+Na$^+$] calculated for C$_{17}$H$_{20}$N$_2$O$_4$Na 339.1321 found 339.1318.

((4aR*,8S*,8aS*)-3-benzyl-8-(phenylethynyl)-8,8a-dihydropyrido[4,3-e][1,4,2]dioxazine-7(4aH)-yl)(phenyl)methanone (2g)

As described in the general procedure, the cycleadduct (1 g) (33 mg, 0.075 mmol) and CuCl (1.5 mg, 0.015 mmol) reacted in DCE (0.50 ml) at 75° C. for 15 h. The subsequent preparation TLC (hexane/AcOEt 7:3, 2 runs) led to the above compound, in yellowish solid form (17 mg, 52%). Melting point=50-55° C.

$^1$H NMR (250 MHz, CD$_3$CN, 65° C.) δ 7.63-7.23 (m, 15 H), 6.71 (d, 1 H, J=8.3 Hz), 5.55 (bs, 1 H), 5.34-5.25 (m, 1 H), 4.83 (dt, 1H, J=8.6, 2.0 Hz,), 4.33-4.23 (m, 1 H), 3.53 (s, 2 H).

¹³C NMR (62.5 MHz, CD₃CN) δ 170.1, 156.8, 136.72, 134.9, 132.8, 132.0, 130.3, 129.7, 129.7, 129.6(x2), 128.8, 128.0, 122.4, 104.1, 85.6, 83.2, 67.6, 66.9, 47.5, 38.5.

HRMS (ESI) m/z [M+Na⁺] calculated for $C_{28}H_{22}N_2O_3Na$ 457.1528 found 457.1528.

1-((4aR*,8S*,8aS*)-3-benzyl-8-phenyl-8,8a-dihydropyrido[4,3-e][1,4,2]dioxazine-7(4aH)-yl)ethanone (2h)

As described in the general procedure, the cycleadduct (1h) (52 mg, 0.15 mmol) and CuCl (3.0 mg, 0.03 mmol) reacted in DCE (1.00 mL) at 75° C. for 16 h. The subsequent flash chromatography (hexane/AcOEt 6:4, Rf=0.26) led to the above compound, in white amorphous solid form (36 mg, 68%).

¹H NMR (250 MHz, CDCl₃) Major rotamer: δ ¹H NMR (250 MHz, CDCl₃) δ 7.59 (d, 1 H, J=9.1 Hz)* and 6.89 (d, 1 H, J=8.9 Hz), 7.42-7.11 (m, 10 H), 5.81 (d, 1 H, J=2.5 Hz) and 5.23 (d, 1 H, J=2.5 Hz)*, 4.80 (dd, J=22.5, 8.6 Hz, 1 H), 4.55 (d, J=18.3 Hz, 1 H), 4.84 (d, 1 H, J=8.7 Hz)* and 4.75 (d, 1 H, J=8.5 Hz), 4.58 (s, 1 H) and 4.51 (s, 1 H)*, 4.09 (bs, 1 H), 3.48 (s, 2 H), 2.28 (s, 3 H) and 2.03 (s, 3 H)*.

¹³C NMR (62.5 MHz, CD₃CN) δ 169.9, 156.6, 137.0* and 136.8, 130.3, 129.9, 129.6, 129.5, 129.3, 128.9, 127.9, 126.8 and 126.6*, 103.8* and 102.7, 69.2, 66.9 and 66.6*, 56.9, 38.5, 21.9.

HRMS (ESI) m/z [M+Na⁺] calculated for $C_{21}H_{20}N_2O_3Na$ 371.1372 found 371.1374.

1-((4aR*,8S*,8aS*)-3,8-diphenyl-8,8a-dihydropyrido[4,3-e][1,4,2]dioxazine-7(4aH)-yl)ethanone (2i)

As described in the general procedure, the cycleadduct (1i) (29 mg, 0.09 mmol) and CuCl (1.7 mg, 0.017 mmol) reacted in DCE (0.57 ml) at 75° C. for 17 h. The subsequent chromatography led to the above compound in almost pure form (23 mg, 75%).

¹H NMR (250 MHz, CDCl₃) δ 7.81-7.75 (m, 2 H), 7.66 (d, 1 H, J=8.7 Hz)* and 6.97 (d, 1 H, J=8.6 Hz), 7.47-7.18 (m, 8 H), 5.92 (d, 1 H, J=2.8 Hz) and 5.33 (d, 1 H, J=2.8 Hz)*, 5.06 (dt, 1 H, J=8.8, 2.0 Hz)* and 4.97 (dt, 1 H, J=8.7, 2.0 Hz), 4.88-4.84 (m, 1 H) and 4.81-4.76 (m, 1 H)*, 4.32-4.26 (m, 1 H), 2.31 (s, 3 H) and 2.06 (s, 3 H)*.

¹³C NMR (62.5 MHz, CDCl₃) δ 169.0* and 168.5, 153.1* and 152.9, 135.7, 135.2, 130.7* and 130.7, 130.2 and 130.1*, 129.7, 129.3, 129.0, 128.4 and 128.3*, 126.3* and 125.8, 102.7* and 102.2, 69.2* and 69.0, 65.9* and 65.7, 59.8, 56.4, 21.8 and 21.7*.

HRMS (ESI) m/z [M+Na⁺] calculated for $C_{20}H_{18}N_2NaO_3$ 357.1215 found 357.1215.

1-((4aR*,8S*,8aS*)-3-benzyl-8-hexyl-8,8a-dihydropyrido[4,3-e][1,4,2]dioxazine-7(4aH)-yl)ethanone (2j)

As described in the general procedure, the cycleadduct (1j) (71 mg, 0.20 mmol) and CuCl (4.0 mg, 0.04 mmol) reacted in DCE (1.32 ml) at 75° C. for 15 h. The subsequent flash chromatography (hexane/AcOEt 3:7, Rf=0.54) led to the above compound, in amorphous solid form (21 mg, 30%).

¹H NMR (250 MHz, CDCl₃) major rotamer δ: 7.38-7.22 (m, 5 H); 6.67 (dt, 1 H, J=1.25, 8.5 Hz); 4.97-4.88 (m, 1 H); 4.77-4.62 (m, 2 H); 3.96 (q, 1 H, J=2.75, 6 Hz); 3.46 (s, 2 H); 2.21 (s, 3 H); 1.39-1.21 (m, 10 H); 0.92-0.80 (m, 3 H).

¹³C NMR (62.5 MHz, CD₃CN) major rotamer δ:169.7; 156.7; 128.1; 127.5; 103.4; 12.3; 67.7; 53.0; 50.2; 38.6; 32.3, 29.7; 26.4; 24.5; 14.4.

HRMS (ESI) m/z [M+Na⁺] calculated for $C_{21}H_{28}N_2O_3Na$ 379.1998 found 379.2000.

Methyl 2-((4aR*,8S*,8aS*)-7-acetyl-3-phenyl-4a,7,8,8a-tetrahydropyrido[4,3-e][1,4,2]dioxazine-8-yl)acetate (2k)

As described in the general procedure, the cycleadduct (1k) (66 mg, 0.20 mmol) and CuCl (4.0 mg, 0.04 mmol) reacted in DCE (1.32 ml) at 75° C. for 15 h. The subsequent flash chromatography (hexane/AcOEt 4:6, Rf=0.35) led to the above compound, in amorphous solid form (28 mg, 42%). Melting point=119-121° C.

¹H NMR (250 MHz, CDCl₃), major rotamer δ 7.79 (dd, 2 H, J=7.9, 1.6 Hz), 7.49-7.32 (m, 3 H), 6.65 (d, 1 H, J=8.6 Hz), 5.30-5.15 (m, 2 H), 4.93 (dt, 1 H, J=8.5, 2.1 Hz), 4.26 (dd, 1 H, J=5.8, 3.0 Hz), 3.71 (s, 3 H), 2.73 (dd, 1 H, J=15.0, 5.7 Hz), 2.43 (dd, 1 H, J=15.0, 9.7 Hz), 2.22 (s, 3 H).

¹³C NMR (62.5 MHz, CDCl₃) δ 170.0, 168.6, 152.9, 130.7, 130.1, 128.4, 127.0, 125.8, 101.7, 66.2 and 66.1*, 52.4, 49.5, 33.9, 21.7. [*minor rotamer].

HRMS (ESI) m/z [M+Na⁺] calculated for $C_{17}H_{18}N_2O_5Na$ 353.1113 found 353.1113.

(4aR*,8aS*)-phenyl 3-phenyl-8,8a-dihydropyrido[4,3-e][1,4,2]dioxazine-7(4aH)-carboxylate (2l)

As described in the general procedure, the cycleadduct (1l) (67 mg, 0.20 mmol) and CuCl (4.0 mg, 0.04 mmol) reacted in DCE (1.32 ml) at 75° C. for 18 h. The subsequent flash chromatography (hexane/AcOEt 7:3, Rf=0.22) led to the above compound, in white solid form (40 mg, 59%). Melting point=130-131° C.

¹H NMR (250 MHz, CDCl₃) δ 7.90-7.80 (m, 2 H), 7.51-7.34 (m, 5 H), 7.30-7.10 (m, 4 H), 5.18 (dd, 1 H, J=8.3, 3.0 Hz)*, 5.12-5.02 (m, 1 H and major rotamer of 5.18), 4.48-4.35 (m, 1 H), 4.24-4.11 (m, 1 H), 4.01 (dd, 1 H, J=14.0, 3.1 Hz)* and 3.83 (dd, 1 H, J=14.1, 2.9 Hz).

¹³C NMR (62.5 MHz, CDCl₃) δ 152.1, 151.5, 150.8 and 150.6*, 130.7 and 130.2*, 129.6 and 129.1*, 128.4, 126.1* and 125.9, 121.6 and 121.6*, 102.3* and 101.9, 66.1 and 65.8*, 65.4* and 65.2, 42.6. [*minor rotamer].

ESI-MS=359.09 (M+Na⁺).

HRMS (ESI) m/z [M+Na⁺] calculated for $C_{19}H_{16}N_2O_4Na$ 359.1008 found 359.1005.

(4aR*,8aS*)-methyl 3-phenyl-8,8a-dihydropyrido[4,3-e][1,4,2]dioxazine-7(4aH)-carboxylate (2m)

As described in the general procedure, the cycleadduct (1m) (50 mg, 0.14 mmol) and CuCl (3.0 mg, 0.03 mmol) reacted in DCE (0.95 ml) at 75° C. for 60 h. The subsequent flash chromatography (hexane/AcOEt 7:3, Rf=0.22) led to the above compound, in yellowish amorphous solid form (40 mg), which was used in the subsequent step without any further purification.

¹H NMR (250 MHz, CD₃CN) δ 7.81-7.65 (m, 2 H), 7.47-7.12 (m, 9 H), 5.57 (d, 1 H, J=2.5 Hz), 5.05-4.93 (m, 1 H), 4.76 (bs, 1 H), 4.34 (d, 1 H, J=2.8 Hz), 3.76 (bs, 3 H).

¹³C NMR (62.5 MHz, CD₃CN) δ 153.6, 137.0, 131.5, 131.5, 130.0, 129.4, 129.2, 128.3, 126.7, 126.5, 69.4, 66.6, 58.7, 54.2.

(4aR*,8S*,8aS*)-methyl 3-benzyl-8-vinyl-8,8a-dihydropyrido[4,3-e][1,4,2]dioxazine-7(4aH)-carboxylate (2n)

As described in the general procedure, the cycleadduct (1n) (193 mg, 0.61 mmol) and CuCl (12.2 mg, 0.123 mmol) reacted in DCE (4.10 ml) at 75° C. for 17 hours. The subsequent flash chromatography (petroleum ether/AcOEt 7:3, Rf=0.23) led to the above compound, in the form of a colourless oil (140 mg, 72.5%).

¹H NMR (250 MHz, CD₃CN, 65° C.) δ 7.39-7.18 (m, 5 H), 6.91 (d, J=8.5 Hz, 1 H), 5.74 (ddd, J=15.7, 10.6, 4.8 Hz, 1 H), 5.26 (d, J=10.5 Hz, 1 H), 5.18 (d, J=17.4 Hz, 1 H), 4.94 (bs, 1 H), 4.79 (bs, 1 H), 4.66 (d, J=8.3 Hz, 1 H), 4.06-3.98 (m, 1 H), 3.75 (s, 3 H) 3.48 (s, 2 H).

$^{13}$C NMR (62.5 MHz, CD$_3$CN) δ 156.5, 154.6, 136.9, 131.5, 129.6, 129.5, 127.9, 127.1, 117.9, 102.1, 67.1, 66.7, 57.3, 54.1, 38.6.

(4aR*,8S*,8aS*)-methyl 3-benzyl-8-cyclohexyl-8,8a-dihydropyrido[4,3-e][1,4,2]dioxazine-7(4aH)-carboxylate (2o)

As described in the general procedure, the cycleadduct (1o) (69 mg, 0.186 mmol) and CuCl (3.7 mg, 0.0373 mmol) reacted in DCE (1.30 ml) at 75° C. for 2 hours. The subsequent flash chromatography (petroleum ether/AcOEt 8:2, Rf=0.25) led to the above compound, in white solid form (40 mg, 58%).

$^1$H NMR (250 MHz, CD$_3$CN) δ 7.39-7.20 (m, 5 H), 6.83 (d, J=7.7 Hz, 1 H), 4.92 (bs, 1 H), 4.70 (d, J=7.5 Hz, 1 H), 4.19 (d, J=8.9 Hz, 1 H), 4.07 (s, 1 H), 3.73 (s, 3 H), 3.47 (s, 2 H), 1.82-1.40 (m, 6 H), 1.32-0.98 (m, 5 H).

$^{13}$C NMR (63 MHz, CD$_3$CN) δ 156.6, 155.3 and 155.2*, 136.9, 129.6, 129.5, 127.8, 127.6 and 127.3*, 103.2* and 102.7, 67.5, 65.5, 60.0, 54.0 and 53.7*, 38.6, 37.9, 30.3, 26.8, 26.6, 26.5. [* minor rotamer]

(4aR*,8S*,8aS*)-methyl 3-benzyl-8-allyl-8,8a-dihydropyrido[4,3-e][1,4,2]dioxazine-7(4aH)-carboxylate (2p)

As described in the general procedure, the cycleadduct (1p) (70 mg, 0.213 mmol) and CuCl (4.2 mg, 0.043 mmol) reacted in DCE (1.4 ml) at 75° C. for 18 hours. The subsequent flash chromatography (hexane/AcOEt 7:3, Rf=0.25) led to the above compound, in the form of a colourless oil (40.4 mg, 57.7%).

$^1$H NMR (250 MHz, CD$_3$CN, 65° C.) δ 7.42-7.20 (m, 5 H), 6.85 (d, J=8.4 Hz, 1 H), 5.96-5.69 (m, 1 H), 5.21-5.02 (m, 2 H), 4.97-4.92 (m, 1 H), 4.74-4.65 (m, 1 H), 4.46 (td, J=7.4, 3.0 Hz, 1 H), 3.96 (dd, J=5.9, 3.0 Hz, 1 H), 3.75 (s, 3 H), 3.49 (s, 2 H), 2.43-2.18 (m, 2 H).

$^{13}$C NMR (62.5 MHz, CD$_3$CN) δ 156.4, 154.6* and 154.3, 136.8, 134.2, 129.6, 129.4, 127.8, 126.7, 118.8, 102.1* and 101.7, 67.0, 66.4, 54.7, 53.9, 38.6, 34.7* and 34.3. [* minor rotamer].

3. Reduction of Dioxazines

3.1 General Procedure for Palladium-Catalysed Allylic Deoxygenation of Dioxazines The dioxazine, the palladium-based catalyst (0.05 equivalents) and the freshly distilled THF were introduced into a 5 ml oven-dried Schlenk tube, in an argon atmosphere. The resulting mixture was cooled to 0° C. and the hydride source was added slowly. Once the dioxazine had disappeared, the reaction was quenched with water, and the aqueous phase was extracted with Et$_2$O. The combined organic layers were dried on MgSO$_4$, concentrated and purified by flash chromatography.

(2S*,3R*)-methyl 2-phenyl-3-((2-phenylacetamido)oxy)-3,4-dihydropyridine-1(2H)-carboxylate (4b) (COMPARATIVE)

As described in the general procedure, the dioxazine (2b) (54.7 mg, 0.15 mmol), Pd(CH$_3$CN)$_2$Cl$_2$ (2.0 mg, 0.0075 mmol), LiBHEt$_3$ (0.9 ml, 0.9 mmol) and THF (0.26 mL) were reacted at 0° C. for 30 minutes. The subsequent flash chromatography (hexane/AcOEt 6:4 Rf=0.15) led to the above compound, in the form of a sticky oil (20 mg, 37%).

$^1$H NMR (250 MHz, CDCl$_3$) 9.04 (bs, 1 H) and 8.60* (bs, 1 H) (replaceable with D$_2$O), 7.43-6.96 (m, 11 H), 5.59 (s, 1 H) and 5.44* (s, 1 H), 4.77 (d, 1 H, J=26.7 Hz), 4.44 (s, 1 H), 3.74 (s, 3 H), 3.60-3.48 (m, 2 H), 2.38-2.11 (m, 1 H), 1.94 (dd, 1 H, J=39.4, 18.4 Hz).

$^{13}$C NMR (62.5 MHz, CDCl$_3$) δ 169.5, 154.7 and 154.4*, 138.4 and 138.2*, 134.2, 129.3, 129.0, 128.9, 127.8, 127.4, 125.7, 125.3, 124.7, 102.6 and 102.0*, 79.9 and 79.4*, 56.4 and 55.8*, 53.5, 31.0, 22.0 and 21.3*. [*minor rotamer].

HRMS (ESI) m/z [M+Na$^+$] calculated for C$_{21}$H$_{22}$N$_2$O$_4$Na 389.1477 found 389.1478.

(5R*,6S*)-methyl 6-phenyl-5-((2-phenylacetamido)oxy)-5,6-dihydropyridine-1(2H)-carboxylate (5b) (COMPARATIVE)

As described in the general procedure, the dioxazine (2b) (54.7 mg, 0.15 mmol), Pd(CH$_3$CN)$_2$Cl$_2$ (2.0 mg, 0.0075 mmol), NaBH$_4$ (35 mg, 0.9 mmol) and THF (0.71 ml) were reacted at 0° C. for 30 minutes. The subsequent flash chromatography (hexane/AcOEt 6:4) led to compound 4b (Rf=0.15) and the above compound, in the form of a sticky oil (Rf=0.22, 7 mg, 13%).

$^1$H NMR (250 MHz, CD$_3$CN, 65° C.) δ 9.21 (bs, 1 H), 7.40-7.23 (m, 10 H), 7.21-7.14 (m, 2 H), 6.16-6.12 (m, 1 H), 6.10 (dd, 1 H, J=3.5, 2.7 Hz), 6.03-5.93 (m, 1 H), 5.67 (s, 1 H), 4.63 (d, 1 H J=5.7 Hz), 4.41-4.38 (m, 1 H), 4.34-4.29 (m, 1 H), 3.71 (s, 3 H), 3.69-3.65 (m, 1 H), 3.59 (dd, 1 H, J=4.3, 2.2 Hz), 3.48 (s, 2 H).

$^{13}$C NMR (62.5 MHz, CDCl$_3$) δ 169.1, 134.1, 132.3, 129.3, 129.0, 128.7, 127.9, 127.4, 127.2, 121.1, 77.4, 53.2, 41.3, 31.0, 29.8.

HRMS (ESI) m/z [M+Na$^+$] calculated for C$_{21}$H$_{22}$N$_2$O$_4$Na 389.1477 found 389.1478.

3.2 General Procedure for the Addition of LiBHEt$_3$ to the Dioxazines

The dioxazine and the freshly distilled THF were introduced into a 5 ml oven-dried Schlenk tube, in an argon atmosphere. The resulting mixture was cooled to 0° C. and a solution of LiBHEt$_3$ (1.0 M in THF, 6.0 equivalents) was added dropwise. Once the dioxazine had disappeared, the reaction was quenched with water, and the aqueous phase was extracted with Et$_2$O. The combined organic layers were dried on MgSO$_4$, concentrated and purified by flash chromatography.

(5S*,9R*)-9-phenyl-3-phenylacetyl-4-oxa-1,3-diazabicyclo[3.3.1]non-6-ene (Ib)

As described in the general procedure, the dioxazine (2b) (54.7 mg, 0.15 mmol), LiBHEt$_3$ (0.90 ml, 0.90 mmol) and THF (0.26 ml) were reacted at 0° C. for 25 minutes. The subsequent flash chromatography (hexane/AcOEt 8:2, Rf=0.17) led to the above compound, in white solid form (47 mg, 98%). Melting point=156-159° C.

$^1$H NMR (250 MHz, CDCl$_3$) δ 7.39-7.20 (m, 10 H), 6.07-5.95 (m, 2 H), 5.61 (d, 1 H, J=13.2 Hz), 4.99-4.89 (m, 1 H), 4.57 (d, 1 H, J=2.2 Hz), 4.48 (d, 1 H, J=13.2 Hz), 3.82 (d, 1 H, J=14.7 Hz), 3.55 (d, 1 H, J=14.7 Hz), 3.45-3.18 (m, 2 H).

$^{13}$C NMR (62.5 MHz, CDCl$_3$) δ 172.3, 137.0, 129.7, 128.7, 128.5, 128.4, 128.0, 127.7, 126.9, 126.8, 119.4, 72.3, 65.7, 59.6, 47.6, 39.8.

HRMS (ESI) m/z [M+Na$^+$] calculated for C$_{20}$H$_{20}$N$_2$O$_2$Na 343.1422 found 343.1421.

(5S*,9R*)-9-ethyl-3-phenylacetyl-4-oxa-1,3-diazabicyclo[3.3.1]non-6-ene (If)

As described in the general procedure, the dioxazine (2f) (50 mg, 0.15 mmol), LiBHEt$_3$ (0.90 ml, 0.90 mmol) and THF (0.26 ml) were reacted at 0° C. for 30 minutes. The subsequent flash chromatography (hexane/AcOEt 5:5, Rf=0.30) led to the above compound, in white solid form (20 mg, 50%). Melting point=68-70° C.

$^1$H NMR (250 MHz, CDCl$_3$) δ 7.45-7.10 (m, 5 H), 6.20-6.13 (m, 1 H), 5.91-5.77 (m, 1 H), 5.48 (d, 1 H, J=13.1 Hz), 4.33-4.19 (m, 2 H), 3.77 (d, 1 H, J=14.7 Hz), 3.52 (dd,

2 H, J=17.3, 8.0 Hz), 3.45-3.31 (m, 2 H), 3.25 (t, 1 H, J=7.4 Hz), 1.41 (ddd, 2 H, J=9.5, 7.4, 2.7 Hz), 0.99 (t, 3 H J=7.4 Hz).

$^{13}$C NMR (62.5 MHz, CDCl$_3$) δ 172.2, 136.5, 135.1, 129.6, 128.5, 126.8, 119.0, 73.6, 65.9, 59.5, 47.5, 39.6, 22.7, 10.6.

FT-IR ν (cm$^{-1}$) 3270.7, 3066.9, 3030.5, 2957.9, 2933.3, 2871.7, 1731.1, 1638.6, 1453.3, 1418.9, 1338.6, 1195.1, 1151.9, 1119.3, 1092.2, 882.3, 704.7.

HRMS (ESI) m/z [M+Na$^+$] calculated for C$_{16}$H$_{20}$N$_2$O$_2$Na 295.1422 found 295.1421.

(5S*,9R*)-3-phenylacetyl-4-oxa-1,3-diazabicyclo[3.3.1]non-6-ene (Ia)

As described in the general procedure, the dioxazine (2a) (53 mg, 0.15 mmol), LiBHEt$_3$ (0.90 ml, 0.90 mmol) and THF (0.26 mL) were reacted at 0° C. for 30 minutes. The subsequent flash chromatography (hexane/AcOEt 5:5+5% Et$_3$N, Rf=0.20) led to the above compound, in white solid form (20 mg, 31%). Melting point=95-98° C.

$^1$H NMR (250 MHz, CDCl$_3$) δ 7.39-7.18 (m, 5 H), 6.22 (dt, 1 H J=10.0, 5.4 Hz), 6.03-5.91 (m, 1 H), 5.44-5.31 (m, 1 H), 4.40-4.33 (m, 1 H), 3.88-3.42 (m, 5 H) 3.0 (d, 1 H, J=13.5 Hz).

$^{13}$C NMR (62.5 MHz, CDCl$_3$) δ 172.1, 136.8, 135.0, 129.6, 128.5, 126.8, 121.1, 70.1, 64.4, 2.0, 50.1, 39.6.

FT-IR ν (cm$^{-1}$) 3033.1, 2929.6, 2893.2, 2857.1, 1653.0, 1453.3, 1415.2, 1386.3, 1337.1, 1278.9, 1217.3, 1145.8, 1012.5, 783.9, 698.6.

HRMS (ESI) m/z [M+Na$^+$] calculated for C$_{14}$H$_{16}$N$_2$O$_2$Na 267.1109 found 267.1110.

(5S*,9R*)-9-phenyl-3-benzoyl-4-oxa-1,3-diazabicyclop[3.3.1]non-6-ene (Im)

As described in the general procedure, the dioxazine (2m) (30 mg, 0.085 mmol), LiBHEt$_3$ (0.51 ml, 0.51 mmol) and THF (0.15 ml) were reacted starting from 0° C. up to room temperature per 18 hours. The subsequent flash chromatography (hexane/AcOEt 5:5, Rf=0.52) led to the above compound in white amorphous solid form (15 mg, 55%). Melting point=98-108° C.

$^1$H NMR (250 MHz, CD$_3$CN, 60° C.) δ 7.65-7.22 (m, 10 H), 5.96 (dt, 1 H, J=10.0 and 2.8 Hz), 5.72-5.55 (m, 2 H), 4.81 (d, 1 H, J=6.3 Hz), 4.71-4.59 (m, 2 H), 3.43-3.19 (m, 2 H).

$^{13}$C NMR (250 MHz, CD$_3$CN, 60° C.) δ 137.5, 131.4, 130.1, 129.2, 129.0, 128.4, 127.0, 121.7, 118.5, 73.5, 60.6, 48.7.

2-phenyl-1-((1R*,5S*,9R*)-9-vinyl-4-oxa-1,3-diazabicyclo[3.3.1]non-6-ene-3-yl)ethanone (In)

As described in the general procedure, the dioxazine (2n) (110 mg, 0.35 mmol), LiBHEt$_3$ (2.1 ml, 2.1 mmol) and THF (0.6 ml) were reacted at 0° C. for 7 hours. The subsequent flash chromatography (petroleum ether/AcOEt 5:5, Rf=0.20) led to the above compound in the form of a colourless oil (27 mg, 27%).

$^1$H NMR (250 MHz, CDCl$_3$) δ 7.36-7.17 (m, 5 H), 6.18-6.08 (m, 1 H), 5.94-5.83 (m, 1 H), 5.69 (ddd, J=17.4, 10.6, 5.4 Hz, 1 H), 5.47 (d, J=13.3 Hz, 1 H), 5.36-5.21 (m, 2 H), 4.37-4.32 (m, 1 H), 4.29 (d, J=13.1 Hz, 1 H), 3.96 (dd, J=3.4, 1.4 Hz, 1 H), 3.75 (d, J=14.8 Hz, 1 H), 3.65-3.53 (m, 1 H), 3.48 (d, J=14.7 Hz, 1 H), 3.44-3.31 (m, 1 H).

$^{13}$C NMR (63 MHz, CDCl$_3$) δ 172.2, 136.7, 135.0, 133.2, 129.6, 128.5, 126.8, 119.0, 118.7, 72.9, 65.2, 59.5, 47.9, 39.6.

2-phenyl-1-(1R*,5S*,9R*)-9-cyclohexyl-4-oxa-1,3-diazabicyclo[3.3.1]non-6-ene-3-yl)ethanone (Io)

As described in the general procedure, the dioxazine (2o) (155 mg, 0.42 mmol), LiBHEt$_3$ (2.5 ml, 2.5 mmol) and THF (0.72 ml) were reacted at 0° C. for 6.5 hours. The subsequent flash chromatography (petroleum ether/AcOEt 7:3, Rf=0.17) led to the above compound in white solid form (19.3 mg, 14%, melting point=139-142° C.) and to the starting material 10 (conversion about 50%, Rf=0.23).

$^1$H NMR (250 MHz, CDCl$_3$) δ 7.36-7.19 (m, 5 H), 6.20-6.10 (m, 1 H), 5.90-5.78 (m, 1 H), 5.45 (d, J=13.0 Hz, 1 H), 4.41 (d, J=5.9 Hz, 1 H), 4.19 (d, J=13.1 Hz, 1 H), 3.75 (d, J=14.7 Hz, 1 H), 3.55-3.26 (m, 3H), 2.95 (d, J=10.3 Hz, 1 H), 1.96 (d, J=12.5 Hz, 1 H), 1.80-1.56 (m, 4 H), 1.38-1.09 (m, 4 H), 1.06-0.78 (m, 2 H).

$^{13}$C NMR (63 MHz, CDCl$_3$) δ 172.1, 137.0, 135.2, 129.6, 128.4, 126.7, 118.9, 72.5, 66.2, 63.0, 47.6, 39.6, 36.3, 30.2, 29.1, 26.5, 25.9, 25.9.

2-phenyl-1-(1R*,5S*,9R*)-9-allyl-4-oxa-1,3-diazabicyclo[3.3.1]non-6-ene-3-yl)ethanone (Ip)

As described in the general procedure, the dioxazine (2p) (115 mg, 0.35 mmol), LiBHEt$_3$ (2.1 ml, 2.1 mmol) and THF (0.6 ml) were reacted at 0° C. for 1.5 hours. The subsequent flash chromatography (hexane/AcOEt 6:4, Rf=0.13) led to the above compound in amorphous solid form (48 mg, 48.2%).

$^1$H NMR (250 MHz, CDCl$_3$) δ 7.36-7.13 (m, 5 H), 6.17 (dt, J=10.0, 2.6 Hz, 1 H), 5.91-5.72 (m, 2 H), 5.45 (d, J=13.1 Hz, 1H), 5.18-5.04 (m, 2 H), 4.30-4.15 (m, 2 H), 3.74 (d, J=14.7 Hz, 1 H), 3.59-3.32 (m, 4H), 2.27-2.02 (m, 2 H).

$^{13}$C NMR (63 MHz, CDCl$_3$) δ 172.1, 136.5, 135.0, 134.3, 129.6, 128.4, 126.7, 118.7, 117.6, 73.1, 65.8, 57.5, 47.5, 39.6, 34.4.

4. Experiment on Biological Activity 4.1 Measurement of the Biological Activity of the 1,3-diaza-4-oxa-[3.3.1]-bicyclic Derivative of Structure (Ib)

The biological activity of the compound (5S*,9R*)-9-phenyl-3-phenylacetyl-4-oxa-1,3-diazabicyclo[3.3.1]non-6-ene (Ib) as a GLP-1 receptor agonist was measured via an ELISA assay specifically modified in order to identify the forms of GLP-1 secreted. The action of the compound of formula Ib (11 μM) as a GLP-1 receptor agonist (mSTC-1 GLP-1 sec CRC) is shown in FIG. 1.

The invention claimed is:
1. Compound having structural formula (I):

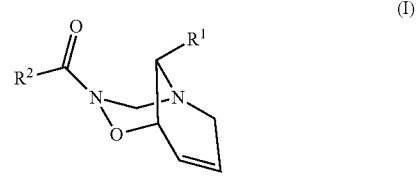

wherein:
R$^1$ is selected from the group consisting of: H, C$_1$-C$_6$ alkyl, vinyl, allyl, cyclohexyl (Chx), 1,2,3-triazole, phenyl optionally substituted by a halogen or by a methoxy functional group, C≡C-Ph, and —CH$_2$—COOCH$_3$; and R$^2$ is selected from the group consisting of:
(i) phenyl or benzyl, optionally substituted by one or more functional groups independently selected from the group consisting of a halogen, a methoxy functional group and —CF$_3$;

(ii) isoxazole;
(iii) pyrrole:

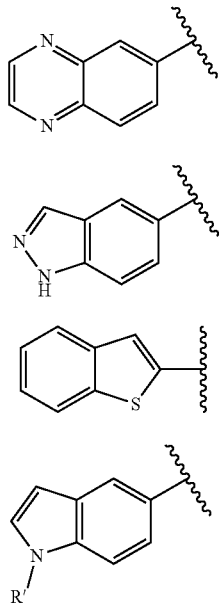

wherein R' is H or methyl wherein R' is H or methyl wherein R' is H or methyl wherein R' is H or methyl.

2. The compound according to claim 1, wherein $R^1$ is selected from the group consisting of hydrogen and phenyl optionally substituted by a halogen or by a methoxy functional group.

3. The compound according to claim 1, wherein $R^2$ is selected from the group consisting of a phenyl or a benzyl, wherein said phenyl or benzyl are optionally substituted by one or more functional groups independently selected from: a halogen, a methoxy functional group and —$CF_3$.

4. The compound according to claim 1, wherein $R^2$ is selected from the group consisting of:

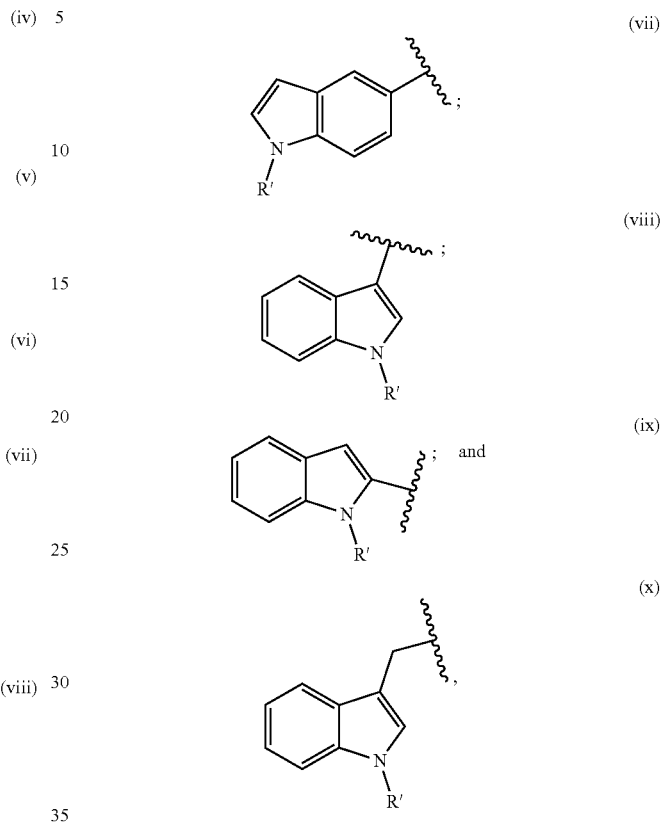

wherein R' is selected from the group consisting of H and methyl.

5. The compound according to claim 1, wherein $R^1$ is phenyl, optionally substituted by a halogen or by the methoxy functional group, and $R^2$ is selected from the group consisting of phenyl and benzyl, wherein said phenyl or benzyl are optionally substituted by a halogen or by the methoxy functional group.

6. The compound according to claim 1, wherein $R^1$ is phenyl, optionally substituted by a halogen or by the methoxy functional group, and $R^2$ is selected from the group consisting of:

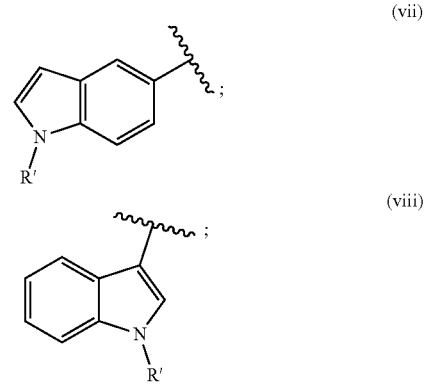

33
-continued
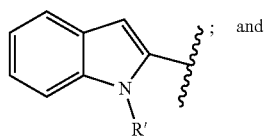 (ix)
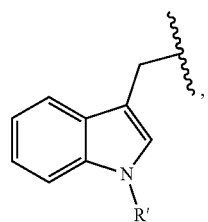 (x)
wherein R' is selected from the group consisting of H or methyl.
7. The compound according to claim 1, wherein R¹ is phenyl, optionally substituted by a halogen or by the methoxy functional group, and R² is pyrrole.
8. The compound according to claim 1, selected from the group consisting of:
34
-continued
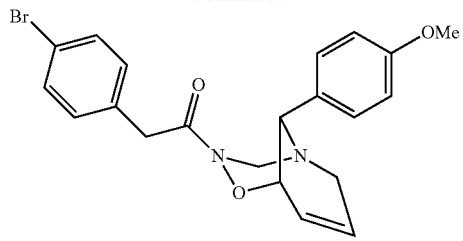
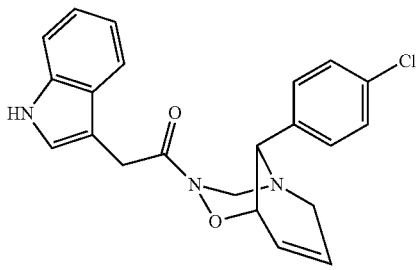
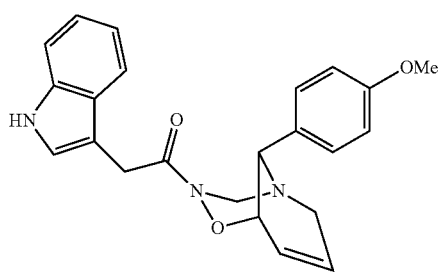
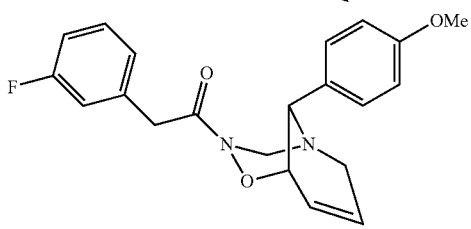
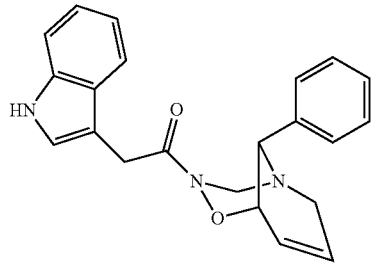
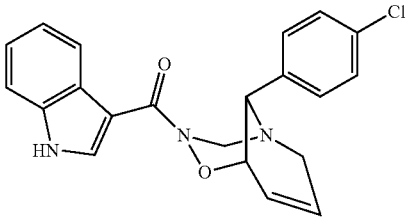
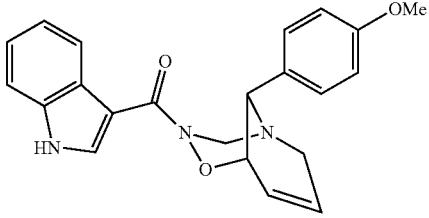

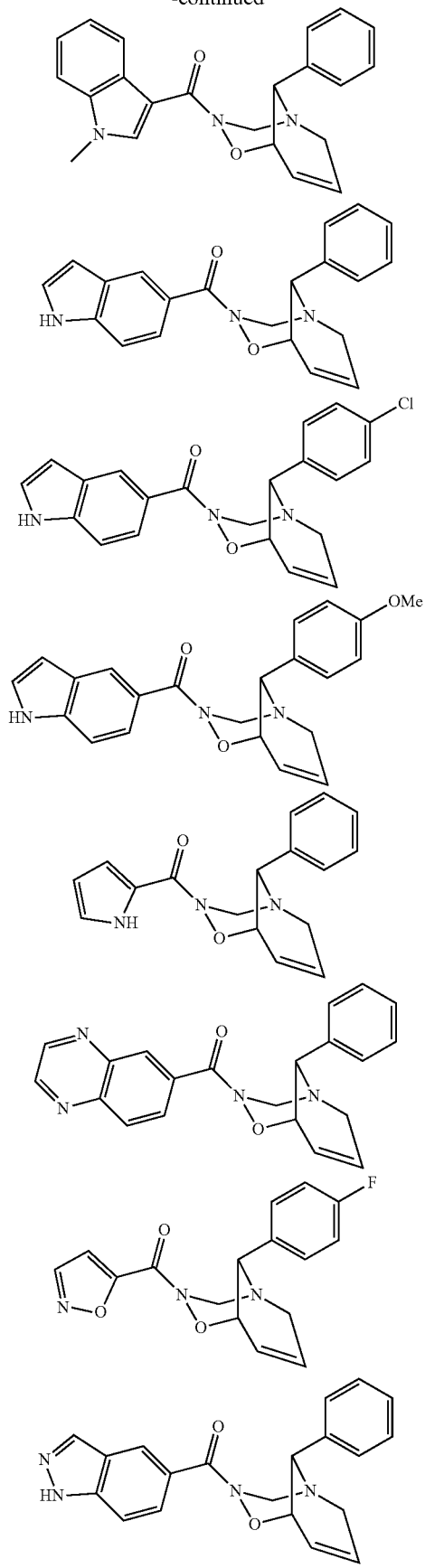
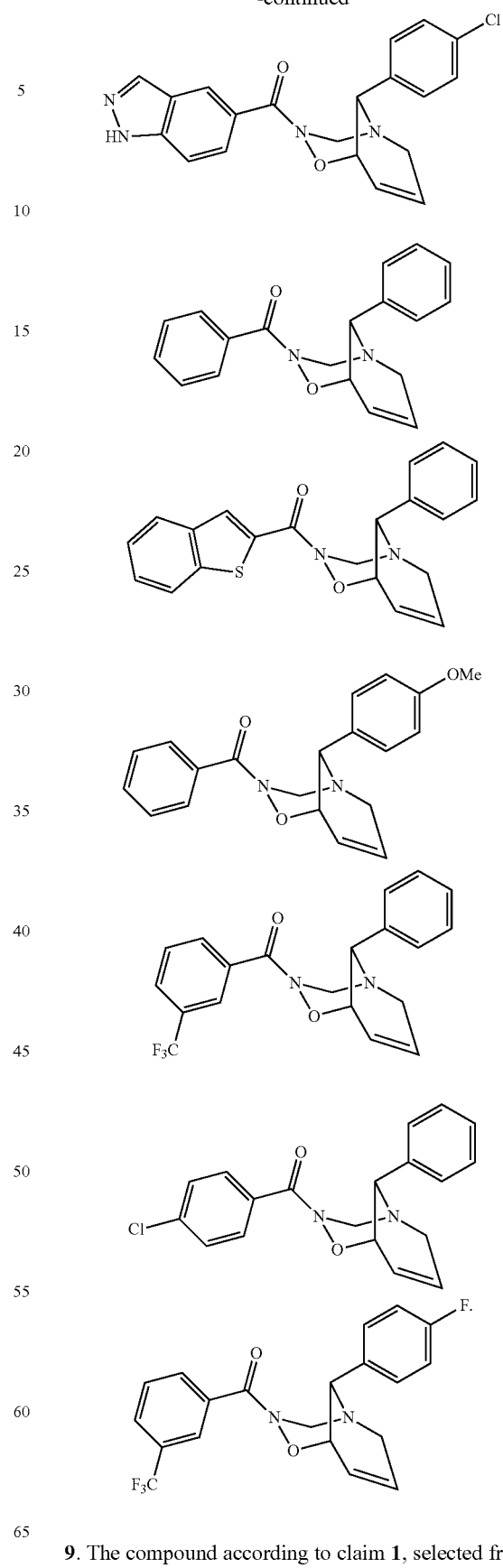
9. The compound according to claim 1, selected from the group consisting of:

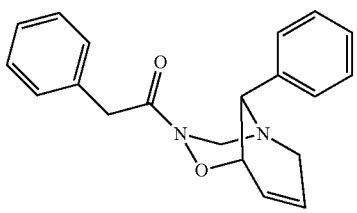 [SMILES: O=C(Cc1ccccc1)N1CN2CC=CC(O1)C2c1ccccc1]
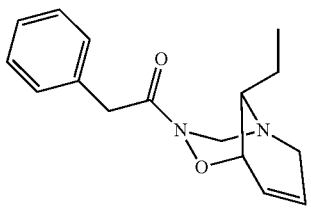
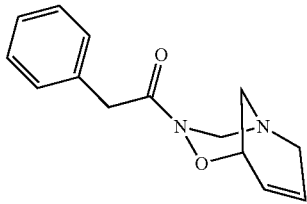
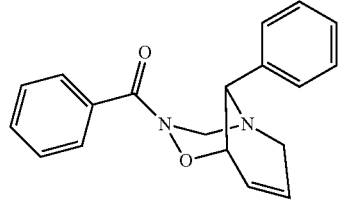
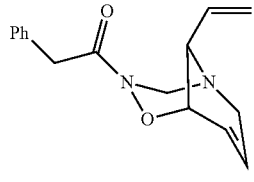
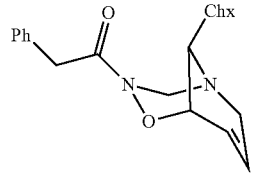
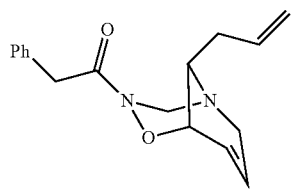

10. The compound according to claim 1, having the structure:

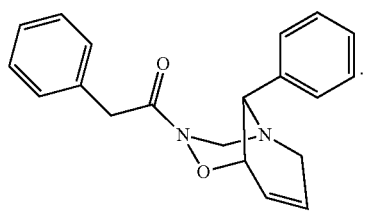 [SMILES: O=C(Cc1ccccc1)N1CN2CC=CC(O1)C2c1ccccc1]

11. A process for the manufacture of a compound of formula (I) according to claim 1, said process comprising: reacting a 4a,7,8,8a-tetrahydropyrido[4,3-e]-1,4,2-dioxazine having formula (2):

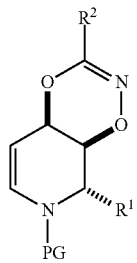

(2)

wherein:

$R^1$ is selected from the group consisting of: H, $C_1$-$C_6$ alkyl, vinyl, allyl, cyclohexyl, 1,2,3-triazole, phenyl optionally substituted by a halogen or by a methoxy functional group, C≡C-Ph, and —$CH_2$—$COOCH_3$; and $R^2$ is selected from the group consisting of:

(i) phenyl or benzyl, optionally substituted by one or more functional groups independently selected from the group consisting of a halogen, a methoxy functional group and —$CF_3$;

(ii) isoxazole;

(iii) pyrrole:

(iv)

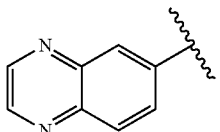

(v)

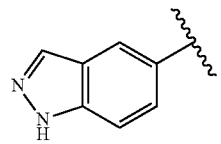

(vi)

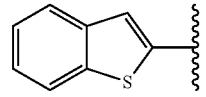

(vii)

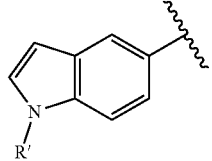

wherein R' is H or methyl (viii)

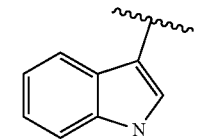

wherein R' is H or methyl

-continued

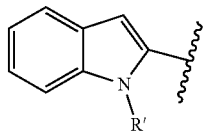

(ix)

wherein R' is H or methyl

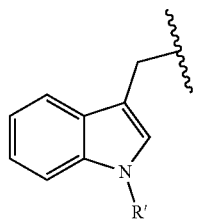

(x)

wherein R' is H or methyl and PG is a protective group comprising a carboxylic functional group, with a hydride selected from the group consisting of: lithium triethylborohydride (LiBHEt$_3$), sodium triethylborohydride (NaBHEt$_3$), and lithium tetrahydroaluminate (LiAlH$_4$), in the presence of tetrahydrofuran, at a temperature comprised between 0° C. and room temperature for a time comprised between 15 minutes and 4 hours.

12. The process according to claim 11, wherein the dioxazine of formula (2) is reacted in the presence of a catalyst selected from the group consisting of: tetrakis(triphenylphosphine)palladium(0) (Pd(PPh$_3$)$_4$) and bis(triphenylphosphine)palladium(II) dichloride ((PPh$_3$)2PdCl$_2$).

13. The process according to claim 11, wherein the dioxazine of formula (2) is prepared by reaction of the corresponding compound of formula (1),

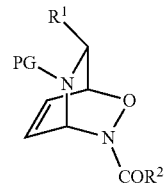

(1)

wherein R$^1$ and R$^2$ are as defined in claim 11, in dichloroethane, at a temperature of 75° C. (±2° C.) and in the presence of CuCl in an amount comprised between 18 mol % and 22 mol %.

14. A method of treating a pathology or condition selected from the group consisting of: diabetes, obesity, dyslipidaemic syndromes, hepatic steatosis and regulation of the sense of satiety with a medicament comprising the compound according to claim 1 or a pharmaceutically acceptable salt thereof, said method comprising
administering a pharmaceutical effective amount of said compound or of said pharmaceutically acceptable salt thereof to a patient in need thereof.

15. The compound according to claim 1, wherein R' is H.

16. The method according to claim 14, wherein said pathology or condition is type 2 diabetes.

* * * * *

UNITED STATES PATENT AND TRADEMARK OFFICE
CERTIFICATE OF CORRECTION

PATENT NO. : 10,913,751 B2  
APPLICATION NO. : 16/616119  
DATED : February 9, 2021  
INVENTOR(S) : Francesco Berti, Mauro Pineschi and Andrea Menichetti It is certified that error appears in the above-identified patent and that said Letters Patent is hereby corrected as shown below:

On the Title Page

Item (72) Inventors:
Andrea Menichetti, Leghorn (IT) should read --"Andrea Menichetti, Livorno (IT)"--

Signed and Sealed this  
Twenty-seventh Day of April, 2021

Drew Hirshfeld  
*Performing the Functions and Duties of the*  
*Under Secretary of Commerce for Intellectual Property and*  
*Director of the United States Patent and Trademark Office*